United States Patent [19]

Orban et al.

[11] Patent Number: 5,130,950
[45] Date of Patent: Jul. 14, 1992

[54] ULTRASONIC MEASUREMENT APPARATUS

[75] Inventors: Jacques Orban; James C. Mayes, both of Sugar Land, Tex.

[73] Assignee: Schlumberger Technology Corporation, Houston, Tex.

[21] Appl. No.: 525,268

[22] Filed: May 16, 1990

[51] Int. Cl.$^5$ .............................................. G01V 1/40
[52] U.S. Cl. ...................................... 367/34; 267/25; 267/86; 267/35; 181/102; 73/155
[58] Field of Search .................. 367/25, 27, 30, 31, 367/34, 35, 86, 87; 181/102, 105; 73/151, 152, 155

[56] References Cited

U.S. PATENT DOCUMENTS

| | | |
|---|---|---|
| 3,673,864 | 7/1972 | Cubberly, Jr. . |
| 3,776,032 | 12/1973 | Vogel . |
| 4,255,798 | 3/1981 | Havira . |
| 4,286,461 | 9/1981 | Bres et al. . |
| 4,527,425 | 7/1985 | Stockton . |
| 4,571,693 | 2/1986 | Birchak et al. . |
| 4,628,725 | 12/1986 | Gouilloud et al. ..................... 73/19 |
| 4,661,933 | 4/1987 | Seeman et al. . |
| 4,665,511 | 5/1987 | Rodney et al. . |
| 4,692,908 | 9/1987 | Ekstrom et al. . |
| 4,780,858 | 10/1988 | Clerke . |
| 4,827,457 | 5/1989 | Seeman et al. . |
| 4,867,264 | 9/1989 | Siegfried . |
| 4,885,723 | 12/1989 | Havira et al. . |
| 4,947,683 | 8/1990 | Minear et al. ......................... 73/155 |
| 4,979,151 | 12/1990 | Ekstrom et al. ..................... 367/35 |

OTHER PUBLICATIONS

"Ultrasonic Velocity as a Probe of Emulsions and Suspensions", by D. J. McClements, et al., Advances in Colloid and Interface Science, 27 (1987), Amsterdam, Netherlands, pp. 285-316.
"Ultrasonic Velocity and Attenuation Measurements in Water-Based Drilling Muds", by A. L. Podio et al., University of Texas at Austin.
"A Dynamic Computer Model of a Kicking Well", by H. V. Nickens, SPE Drilling Engineering, Jun. 1987.
"Delta Flow: An Accurate, Reliable System for Detecting Kicks and Loss of Circulation During Drilling", by J. M. Speers et al., SPE Drilling Engineering, Dec. 1987.
"Theoretical and Experimental Development of the Ultrasonic Diplog SM System", by B. B. Strozzeski, et al., SPWLA Thirtieth Annual Logging ... Symposium, Jun. 11-14, 1989.
"MWD Monitoring of Gas Kicks Ensures Safer Drilling", by Robert Desbrandes et al., Petroleum Engineer International, Jul. 1987.
"Instrumentation Requirements for Kick Detection in Deep Water", by L. D. Maus, et al., Journal of Petroleum Technology, Aug. 1979.

Primary Examiner—Ian J. Lobo
Attorney, Agent, or Firm—Gary L. Bush; John J. Ryberg

[57] ABSTRACT

Pulse echo apparatus and methods are disclosed for measuring characteristics of a borehole while it is being drilled. A component of a bottomhole assembly, preferably a drilling collar, is provided with one or more ultra-sonic transceivers. A pulse echo sensor of the transceiver is preferably placed in a stabilizer fin of the collar, but may also be placed in the wall of the collar, preferably close to a stabilizing fin. Electronic processing and control circuitry for the pulse-echo sensor is provided in an electronic module placed within such collar. Such pulse echo apparatus, which preferably includes two diametrically opposed transceivers, generates signals from which standoff from a borehole wall may be determined. A method and apparatus are provided for measuring standoff and borehole diameter in the presence of drilling cuttings entrained in the drilling fluid. In a preferred embodiment, such signals are assessed by the electronic processing and control circuity to determine if gas has entered borehole. Three methods and apparatus are provided for such gas entry determination. The first relies on measurement of sonic impedance of the drilling fluid by assessing the amplitude of an echo from an interface between the drilling fluid and a delay-line placed outwardly of a ceramic sensor. The second relies on measurement of drilling fluid attenuation of a borehole wall echo. The third relies on measurement of the phase of oscillations of echoes to identify large gas bubbles entries. The pulse-echo sensor includes a sensor stack including a backing element, a piezo-electric ceramic disk, and a delay-line.

20 Claims, 8 Drawing Sheets

*FIG. 3B*
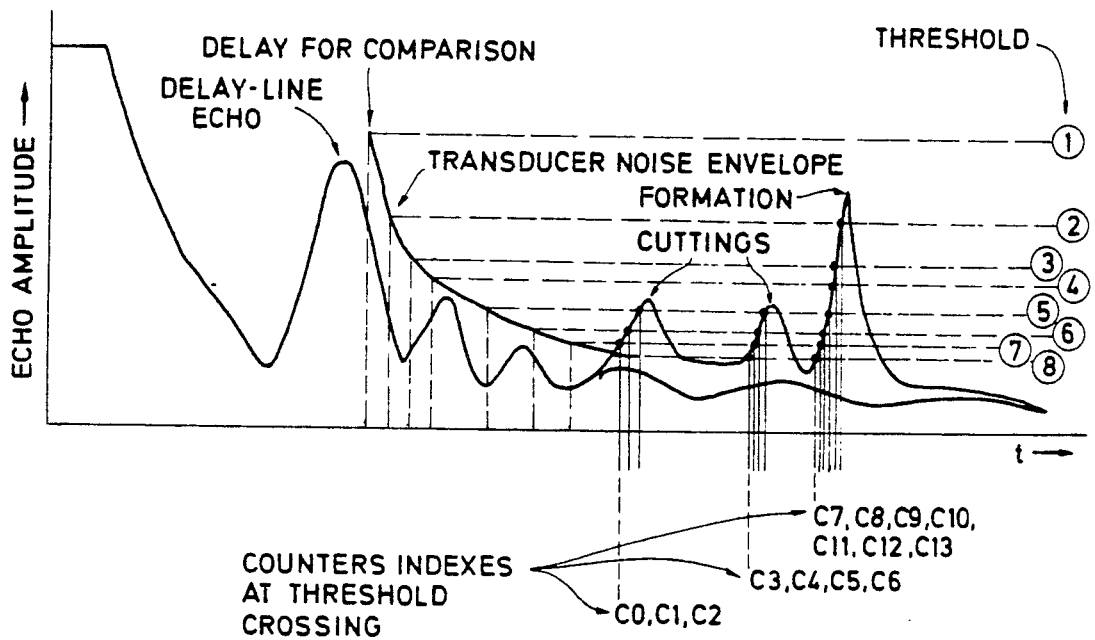
*FIG. 9C*  *FIG. 9D*
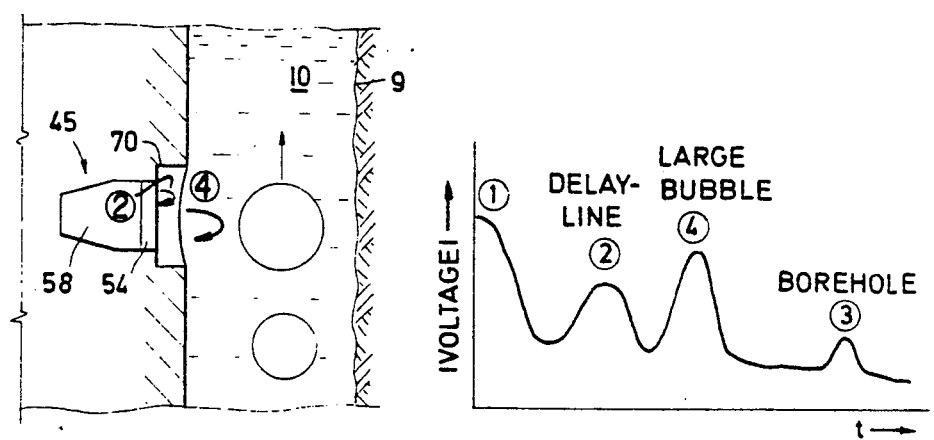

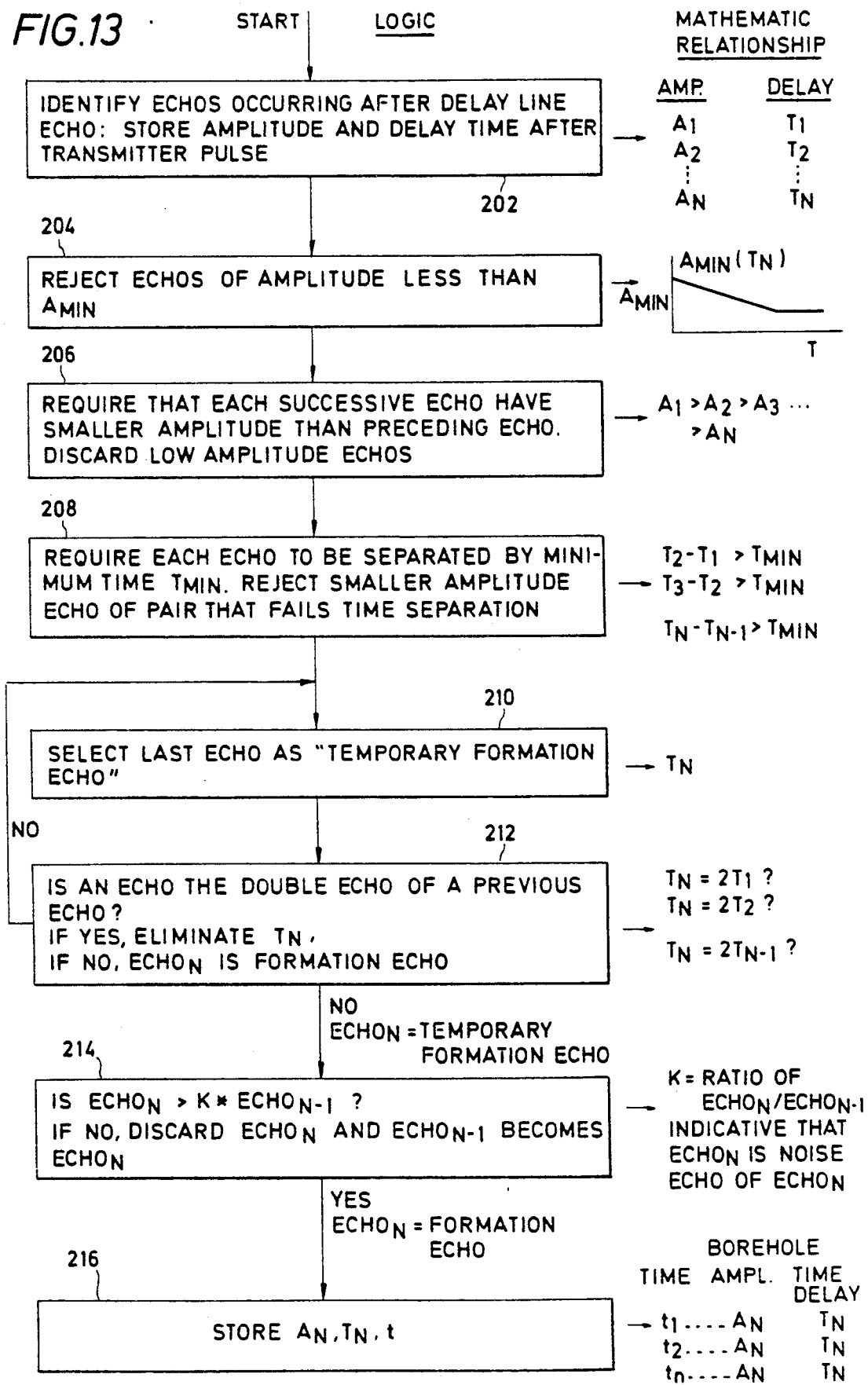

ULTRASONIC MEASUREMENT APPARATUS

TECHNICAL FIELD

This invention relates generally to the ultra-sonic measurement of borehole characteristics. More particularly this invention relates to, apparatus and methods of ultra-sonic measuring of borehole characteristics while a well is being drilled. Still more particularly the invention relates to measurement of borehole diameter and gas influx of a borehole while it is being drilled. The invention relates also to a particular ultra-sonic sensor incorporated in the apparatus for measuring such characteristics.

BACKGROUND OF THE INVENTION

The apparatus and methods of this invention provide for the measurement of borehole diameter and for the detection of gas influx while a well is being drilled.

Borehole Caliper Measurement

Knowledge of a borehole's diameter while it is being drilled is important to the driller because remedial action may be taken by the driller in real time, preventing the delay inherent in tripping the drill string and conducting open-hole logging activities. If the diameter of the borehole is over-gauge, such fact may indicate that there is inappropriate mud flow, or an improper mud chemical characteristic or that the well hydrostatic pressure is too low, or that there is some other source of well-bore instability. If the diameter of the borehole is below gauge or nominal size, such fact may indicate that the bit is worn and should be replaced so as to obviate the need for later well reaming activities.

Well bore diameter instability increases the risk that the drilling string may become stuck downhole. Stuck pipe implies an expensive and time consuming fishing job to recover the string or deviation of the hole after the loss of the bottom of the drilling string. Well bore diameter variation information is important to the driller in real time so that remedial action may be taken.

Well bore diameter as a function of depth is also important information for a driller where the borehole must be kept open for an extended portion of time. Monitoring of well bore diameter when the drill string is tripped out of the borehole provides information to the driller regarding proper drilling fluid characteristics as they relate to formation properties.

Knowledge of borehole diameter also aids the driller when deviated holes are being drilled. When a borehole is out of gauge, directional drilling is difficult because the drill-string, bottom-hole assembly, and collar stabilizers do not contact the borehole walls as predicted by the driller. Real time knowledge of borehole diameter provides information on which to base directional drilling decisions. Such decisions may eliminate the need for tripping the string so as to modify the bottom-hole assembly to correct a hole curvature deviation problem.

Real time knowledge of well bore diameter is important in logging while drilling (LWD) operations. Certain measurements, especially nuclear measurements of the formation, are sensitive to borehole diameter. Knowledge of the well bore diameter under certain circumstances can be critical for validating or correcting such measurements.

U.S. Pat. No. 4,665,511 describes a system for measuring the diameter of a well while it is being drilled. Such system provides ultra-sonic transducers on diametrically opposed sides of a drilling sub. It relies on the reception of echoes of emitted pulses from the borehole walls, but such reception is often confused by the presence of drill cuttings in the drilling fluid. Measurement of the diameter of a borehole using the apparatus of this patent may also be inaccurate where the sub is not centralized with the axis of the borehole. Such inaccuracy may occur where the drilling sub is adjacent the borehole wall and the diameter of the sub is smaller than the diameter of the borehole. Under such conditions, the "diameter" sensed by the drilling sub is in reality a chord of the borehole which is smaller than the actual borehole diameter.

Identification of objects of the invention with respect to borehole caliper measurement aspects of the invention are described below after other aspects of the invention are described.

Borehole Gas Influx Detection

Gas influx, or a "kick" into the borehole, is a serious hazard in the drilling art since kicks, if uncontrolled, can cause well blowouts. Well blowouts may result in loss of life, damage to expensive drilling equipment, waste of natural resources, and damage to the environment.

Prior art kick detection while drilling has typically involved observation of the mud flow rate and/or mud pit volume. Accordingly, almost every rig which uses drilling fluid or mud to control the pressure in the borehole has some form of pit-level indicating device that indicates a gain or loss of mud. A mud pit-level indicating and recording device, such as a chart, is usually located in a position so that the driller can see the chart while drilling is occurring. When a kick occurs, the surface pressure required to contain it largely depends upon closing well-head BOPs quickly and retaining as much mud as possible in the well.

Flow meters showing relative changes in return mud flow have also been used as a kick warning device, because mud hold-up in solids control devices, degassers, and mixing equipment affects average pit-level. Such fluctuations in pit-level due to such factors recur periodically during drilling and may occur simultaneously with a kick. When such conditions are present, a return flow rate may be the first indication of a kick.

To determine kicks as early as possible while drilling, the driller typically uses instantaneous charts of average volume of the mud pit, mud gained or lost from the pit, and return flow rate. Preferably, the pit volume and return flow rate is displayed (and possibly recorded by means of a graph) on the drilling floor so that trends can be observed. As soon as an unexpected change in the trends occurs, a driller checks for a kick condition.

These prior art kick detection techniques for land drilling operations typically require ten to twenty minutes of delay from the time a gas influx occurs at the bottom of the well until pit volume or return mud flow rate is sufficiently affected to be detected. For offshore operations such delay may be twice that for land operations.

Because a kick can lead to a blowout with possible disastrous results, prior attempts have been made to obtain information as to gas influx into the borehole before such influx affects pit mud volume or return flow rate. U.S. Pat. No. 4,571,603 discloses apparatus for measuring characteristics of drilling mud with a probe adapted for inclusion in a drill string member. Such probe includes an ultra-sonic transducer which serves to emit sonic pulses and receive echo signals. A gap in the path of the ultra-sonic pulses is provided so that drilling fluid may enter the gap. Reflections from a near surface of the gap and from a far surface of the gap are analyzed. Such analysis is said to permit determination of the speed of sound of the drilling fluid, sonic attenuation, the product of fluid density and compressibility, viscosity etc.

Such patent does not describe a practical system in a down-hole measuring-while-drilling environment, because the probe gap may quickly become caked or filled with mud particulate. Such caking of the gap renders the probe inoperable for determining characteristics of downhole drilling fluid. The apparatus and method also ignores the presence of cuttings in the drilling fluid which affect reflections received by an ultra-sonic transducer.

Identification of objects of the invention with respect to gas influx or kick detection measurements of the invention are described below.

Ultra-sonic Sensor for a Measurement While Drilling Environment

The drilling environment in which an ultra-sonic sensor must function, if it is to measure borehole and drilling fluid characteristics while drilling, is truly daunting. Shocks and vibrations up to 650 G's/mSec of the drill string render prior art ultra-sonic sensor assemblies useless. Measurement while drilling sensors must survive for several days, unlike wireline logging sensors, because drilling continues for such time length. Noise created by high speed drilling fluid through drilling tools and by tools impacting rock formations must be eliminated in signal processing. In addition, the sensors must be capable of withstanding pressures up to 20,000 psi and temperatures up to 150° C. as well as mechanical abrasion and direct hits on the sensor face.

Identification of objects of the invention with respect to the ultra-sonic sensor aspects of the invention are described below.

IDENTIFICATION OF OBJECTS OF THE INVENTION

Borehole Caliper Measurement

It is a primary object of the invention to measure-while-drilling the borehole diameter and tool standoff by pulse-echo techniques by recognizing and eliminating reflections from cuttings in the drilling fluid returning to the surface between the tool and the borehole wall.

It is another object of the invention to measure-while-drilling borehole diameter and tool standoff by pulse echo techniques and to statistically process such measurements downhole to significantly improve the accuracy of such measurements.

It is still another object of the invention to mount a pulse echo sensor on or near a stabilizer of a drilling tool to minimize inaccuracies caused by such tool not being centralized with the axis of the borehole.

It is still another object of the invention to measure while drilling borehole diameter and tool standoff by pulse echo techniques and to transmit a signal representative of same to the surface.

Borehole Gas Influx Detection

Another primary object of the invention is to provide a practical and reliable method and apparatus for measuring gas influx into a well while it is being drilling and telemetering a signal representative of that measurement to the surface.

Another object of the invention is to provide a method and apparatus for detecting gas influx into a borehole even though drill cuttings are entrained within the borehole fluid.

Another object of the invention is to provide a method and tool for assessing gas influx into a borehole by pulse-echo measurement of flowing drilling fluid as it returns to the surface in the annulus between the tool and the borehole.

Another object of the invention is to provide alternative techniques for assessing gas influx into a borehole and using such techniques as redundant indicators of gas influx.

Another object of the invention is to provide apparatus and method for measuring the sonic impedance of drilling fluid in a borehole by assessing echoes from the interface between a delay line and such drilling fluid.

Another object of the invention is to provide apparatus and method for measuring sonic attenuation of drilling fluid in the borehole by assessing echoes from the borehole wall.

Another object of the invention is to provide apparatus and method for detection of large bubbles in the borehole drilling fluid.

Ultra-sonic Sensor for a Measuring-while-drilling Environment

Another primary object of the invention is to provide an ultra-sonic sensor and associated electronics and tool in which it is placed which can survive extremely harsh forces, temperatures, pressures and noise present in a borehole while it is being drilled.

Another object of the invention is to provide a tool structure and ultra-sonic sensor which are not subject to mud caking while measuring characteristics of drilling fluid as it flows past the sensor.

Another object of the invention is to provide a sensor assembly which includes a delay line including a structure for focusing ultra-sonic pulses toward the borehole.

Another object of the invention is to provide a sensor assembly which creates a smooth outside profile with a downhole drilling tool to prevent caking of drilling fluid particulate in the path of ultra-sonic pulses and echoes.

Another object of the invention is to provide a mounting structure for a pulse echo sensor assembly in a downhole drilling tool to protect the assembly from extremely high shock forces.

Another object of the invention is to provide a pulse echo sensor assembly to accommodate thermal expansion of components due to extremely high downhole temperatures.

Another object of the invention is to provide a pulse echo sensor assembly which prevents fluid invasion into sensor components even under extremely high pressures of a borehole environment.

Another object of the invention is to provide mechanical noise rejection structures to reduce noise generated by high velocity mud flow through the drilling tool, thereby allowing a large range of signal detection after attenuation.

Still another object of the invention is to provide electronic control and processing circuits for emitting and receiving ultra-sonic pulses and echoes and for processing echo data to generate caliper and gas influx signals.

SUMMARY OF THE INVENTION

The objects identified above, as well as other advantages and features of the invention, are preferably incorporated in an ultra-sonic system disposed within a measuring-while-drilling (MWD) or logging-while-drilling (LWD) apparatus to perform hole caliper monitoring and/or gas influx detection.

The system includes an ultra-sonic transceiver installed in a drill collar. Such drill collar functions in the drilling process to put weight on the bit, etc. In other words, it functions as an ordinary drill collar independent of the MWD measuring apparatus described here. A second identical transceiver is preferably installed at the azimuthal opposed position of the first transceiver in the same collar, and at the same axial position. This second transceiver improves the reliability of gas detection and the caliper accuracy.

The transceiver is designed to generate an ultrasonic pulse in the mud in the direction perpendicular to the face of the collar. The wave pulse travels through the mud, reflects from the formation surface and comes back to the same transceiver which, after the ultra-sonic pulse has been emitted, acts as a receiver. The travel time of the pulse in the mud is proportional to the standoff distance of the tool from the borehole wall.

The transceiver includes a solid "delay-line" between a ceramic sensor and the drilling fluid. Such "delay-line" reflects a portion of the emitted sonic pulse back to the sensor from the interface of the delay line and the mud. The amplitude of such pulse is related to the sonic impedance of the mud. Such sonic impedance depends directly on the amount of gas in the mud, i.e., it depends on the density of the mud. Accordingly, the sonic impedance of the mud is an important parameter for downhole gas influx detection.

Providing a delay-line in front of the sonic sensor advantageously allows echo detection where the tool is close to the borehole. Furthermore, such delay-line provides focusing, protection of the sensor, and other mechanical functions as described below.

In addition to the transceiver, the drill string collar includes electronic circuits, a microprocessor, and memory circuits to control the sensor and to receive echo signals and process them. Processed signals may be stored in down-hole memory (caliper for example), or may be transmitted to the surface by a standard measuring-while-drilling mud pulse device and method. Both methods (storage and transmission) can be used simultaneously. Alternatively, the caliper signals may be stored and the gas influx signals transmitted to the surface in real time.

Borehole Caliper Measurement

The apparatus of the invention provides a tool standoff measurement to determine the hole diameter when the tool is rotating (which is the normal case during drilling), or when the tool is stationary. When the tool is rotating, the transceiver sends the sonic pulse through the mud gap distance between the tool and borehole wall. Such gap varies with the tool rotation. The measured standoffs are accumulated for statistical processing, and the average hole diameter is calculated after several turns. Several standoff measurements are preferably evaluated each second. Because the typical drill string rotation speed is between about 50 to 200 RPM, an average accumulation time from about 10 to about 60 seconds creates enough data for accurate averaging.

Providing a second transceiver diametrically opposed from the first improves the diameter measurement when the tool axis moves from side to side in the well-bore during drilling. One transceiver measures the standoff on its side. Then immediately thereafter the other transceiver measures the standoff on the other side of the tool. An instantaneous firing of both transceivers is not required as long as tool movement in the time between the two transceiver measurements is small.

The hole diameter is determined by adding the tool diameter to the standoffs measured on successive firings. A number of borehole diameter determinations are accumulated and averaged to produce a borehole measurement. Additional processing according to the invention relates to processing for rejection of false echoes. Such processing identifies formation echoes which occur after echoes from drilling cuttings in the drilling fluid. The processing also distinguishes formation echoes from its multiple arrivals, and from sensor noise.

An important feature of a particularly preferred embodiment of the present invention is to mount the transceiver near a stabilizer or on the stabilizer blades of the collar. Such placement of the transceiver improves the accuracy of the caliper measurement.

Borehole Gas Influx Detection

Gas influx or a "kick" is detected by two techniques which may be used individually or together to confirm each other. The first technique is to measure the sonic impedance of the mud in the borehole while the borehole is being drilled. The other technique is to measure the attenuation of the mud in the borehole while it is being drilled.

To measure mud impedance, the transceiver includes a delay-line in front of the sensor. When a sonic pulse is emitted from the sensor, it reaches the front face of the delay-line. Part of the sound pulse is transmitted into the drilling fluid. The other part is reflected back toward the sensor. Because the reflection coefficient depends on the mud impedance, the amplitude measurement of the reflected signal is representative of mud impedance as a function of time. The occurrence of a gas influx can be determined by monitoring variations in the measured mud impedance versus time, or alternatively by comparing the measured mud impedence to a reference measurement of the impedance of "clean" mud.

Mud attenuation is defined as the signal amplitude reduction with an increased standoff. Measurement of mud attenuation requires several measurements of the amplitude of the sonic echo signal after it has travelled different standoff distances in the mud. Such echo for this invention is the borehole echo which returns to the sensor after reflection from the borehole wall. It is important that the emitted pulse amplitude and frequency be maintained substantially constant for all the several measurements of the attenuation. For a predetermined measurement period, several standoff values are measured as the tool is moving in the well-bore. For each standoff, the amplitude of the formation echo is measured. Then, the logarithm values of this amplitude versus the standoffs are stored in a table. The slope of a line fit to the logarithm amplitude values is determined.

A major advantage of the method and apparatus of the invention over other methods to monitor mud attenuation is the performance of the measurement through a mud sample which is part of the drilling fluid flow of the annulus between borehole wall and the drilling tool. Accordingly, there is no risk of plugging a "gap" measurement with cuttings, drilling debris, or sticky clay, because the mud flow and the tool movement through the mud clean the sensor face.

Ultra-sonic Sensor for a Measurement While Drilling Environment

The ultra-sonic sensor assembly of the invention is adapted for placement in the wall or stabilizer fin of a drilling collar which is placed above the drilling bit of a down-hole drilling assembly. The ultra-sonic sensor assembly includes a sensor stack having an inner sound absorbing backing element, a piezo-electric ceramic disk stacked outwardly adjacent the backing element, and a delay-line. Such delay-line is fabricated of rigid plastic material and is disposed outwardly of the ceramic disk. Such delay-line includes an outwardly facing depression for focusing an ultra-sonic pulse into the drilling mud toward the borehole wall. An elastomer or epoxy fills the depression to present a smooth face to the flowing mud and the borehole wall.

The sensor assembly includes electrodes attached to the outer and inner surfaces of the ceramic disk and connector pins for connecting the assembly to an electronics module disposed within the drilling collar. Such electronics module includes control and processing circuitry and stored logic for emitting ultra-sonic pulses via the ceramic disk sensor and for generating echo signals representative of echoes of such pulses which return to the disk sensor. Such electronic module also preferably includes a source of electrical energy (such as a battery or source of d.c. current from a MWD tool) and downhole memory for storing signals as a function of time. It interfaces with an MWD telemetry module for transmitting measurement information to the surface while drilling in real time.

The backing element of the ultra-sonic sensor assembly is characterized by a solid portion (preferably, but not necessarily cylindrical in shape) disposed inwardly adjacent to the ceramic disk and a frusto-conical portion disposed inwardly adjacent the solid cylindrical portion.

The sensor stack includes a rubber jacket disposed around the backing material, the ceramic disk, and a matching layer disposed outwardly adjacent the ceramic disk. A tube of elastomeric material is placed between the rubber jacket and a metallic cup in which the sensor stack is placed. The delay-line is spring mounted in the cup outwardly of the rubber jacket and elastomeric tube which surround the sensor stack.

Two sources of noise are present in the vicinity of the sensor stack of the tool. The first can be characterized as drilling noise which is of a lower frequency band than that of the acoustic pulse-echo apparatus of the sensor. The second is pumping noise which is characterized by a frequency band which extends into the frequency range of the pulse-echo apparatus.

Pumping noise is mechanically filtered not only by the rubber jacket surrounding the sensor stack, but also by a filter ring mounted radially outwardly of the ceramic disk about the rubber jacket. The backing element is shock protected by rubber packing between it and the elastomeric sleeve which envelops the stack.

Drilling noise, which may be of extremely high amplitude, is partially mechanically filtered by the rubber jacket and filter ring described above and partially electronically filtered. Electronic filtering is achieved by an electronic high-pass filter placed prior to signal amplification to avoid amplifier saturation which could mask ultra-sonic signal detection during amplifier saturation and recovery time.

BRIEF DESCRIPTION OF THE DRAWINGS

The objects, advantages and features of the invention will become more apparent by reference to the drawings which are appended hereto and wherein like numerals indicate like parts and wherein an illustrative embodiment of the invention is shown, of which:

FIG. 3B illustrates a stored program implementation of a firing/threshold-/counter apparatus and method to digitize filtered echo signals;

FIGS. 9C and 9D are illustrations similar to those of FIGS. 9A and 9B but for the case of large gas bubbles in the drilling fluid, resulting in a large amplitude echo which is sensed after the delay-line/drilling fluid echo;

FIG. 13 is a flow diagram illustrative of logic steps performed by a computer in the electronics module of the tool to identify borehole echoes and delay-line echoes under the conditions illustrated in FIGS. 6A, 6B to 12;

DESCRIPTION OF THE INVENTION

Introduction

Figures 1, 1A:
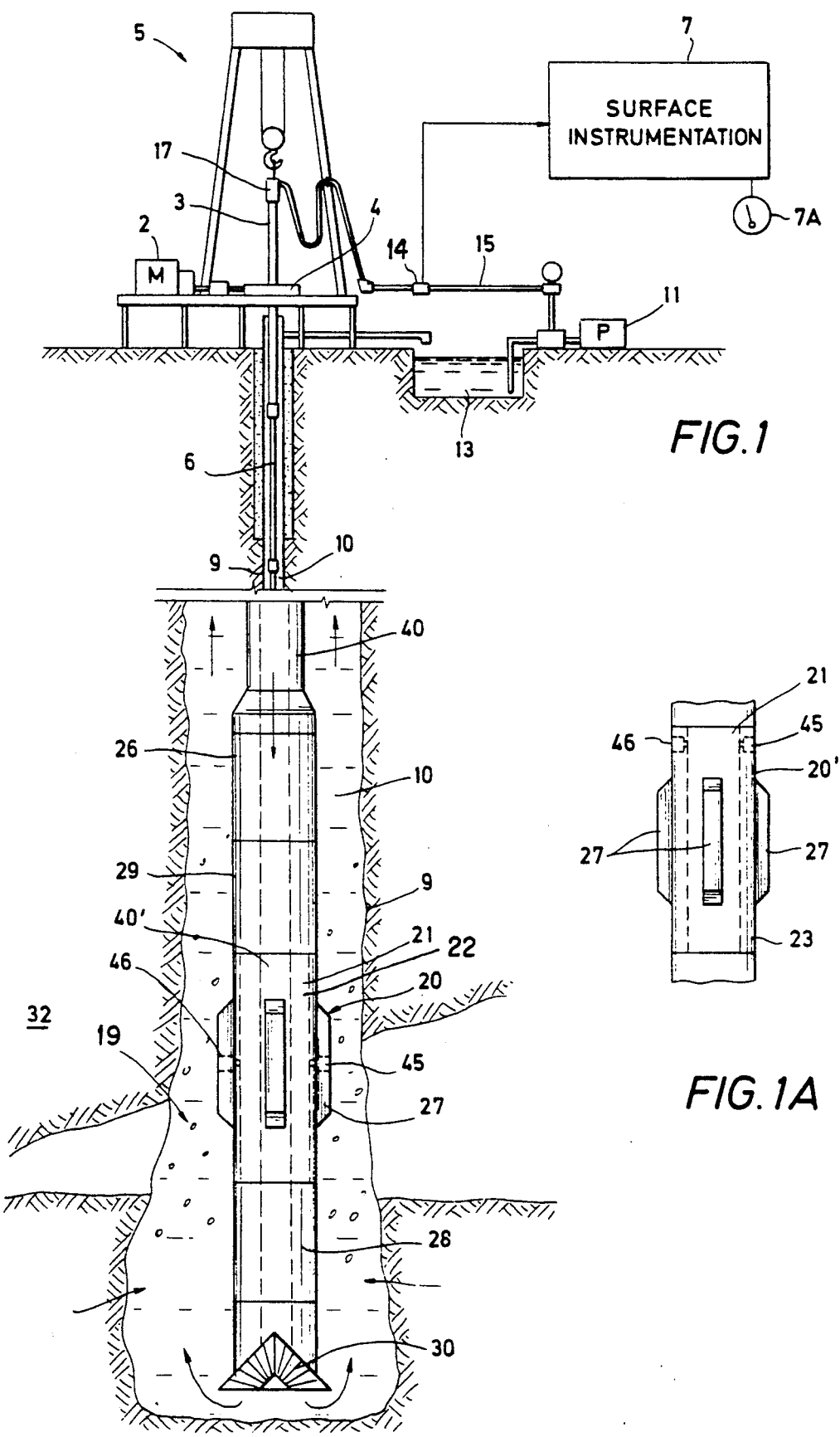
FIG. 1 illustrates an ultra-sonic measurement tool placed in a drill string of a rotary drilling system, where the tool measures borehole diameter and fluid influx while the drill string is turning or stationary.
FIG. 1A illustrates an alternative placement of an ultra-sonic sensor assembly in the wall of a drill collar, rather than in stabilizing fins of such drill collar.

FIG. 1 illustrates a rotary drilling rig system 5 having apparatus for detection, while drilling, of borehole diameter and for gas influx into the borehole. Downhole measurements are conducted by instruments disposed in drill collar 20. Such measurements may be stored in memory apparatus of the downhole instruments, or may be telemetered to the surface via conventional measuring-while-drilling telemetering apparatus and techniques. For that purpose, an MWD tool sub, schematically illustrated as tool 29, receives signals from instruments of collar 20, and telemeters them via the mud path of drill string 6 and ultimately to surface instrumentation 7 via a pressure sensor 14 in stand pipe 15.

Drilling rig 5 includes a motor 2 which turns a kelly 3 by means of a rotary table 4. A drill string 6 includes sections of drill pipe connected end-to-end to the kelly and turned thereby. A plurality of drill collars such as collars 26 and 28 and collar 20 of this invention, as well as one or more MWD tools 29 are attached to the drilling string 6. Such collars and tool form a bottom hole drilling assembly between the drill string 6 of drill pipe and the drilling bit 30.

As the drill string 6 and the bottom hole assembly turn, the drill bit 30 bores the borehole 9. An annulus 10 is defined between the outside of the drill string 6 and bottom hole assembly and the borehole 9 through earth formations 32.

Drilling fluid or "mud" is forced by pump 11 from mud pit 13 via stand pipe 15 and revolving injector head 17 through the hollow center of kelly 3 and drill string 6 to the bit 30. Such mud acts to lubricate drill bit 30 and to carry borehole cuttings or chips upwardly to the surface via annulus 10. The mud is returned to mud pit 13 where it is separated from borehole cuttings and the like, degassed, and returned for application again to the drill string.

The tool 20 of the invention includes at least one ultra-sonic transceiver 45, but preferable also a second transceiver 46 placed diametrically opposed from the first, for measuring characteristics of the borehole while it is being drilled.

Such measurements are preferably conducted while the borehole is being drilled, but they may be made with the drill string and the bottom hole assembly in the borehole while the bit, bottom hole assembly and drill string are not turning. Such measurements may even be conducted while the entire string, bottom hole assembly and bit are being tripped to and from the bottom of the borehole, but the primary use of the measurement is while the borehole is being drilled. As mentioned above, such characteristics of the borehole 9 may be telemetered to the surface via MWD telemetering tool 29 and the internal mud passage of drill string 6, or they may be recorded and stored downhole and read out at the surface after the drill string has been removed from the borehole as will be explained below.

The transceivers 45, 46 are preferably mounted on stabilizer fins 27 of collar 20 or may be mounted in the cylindrical wall 23 of the collar 20' as illustrated in FIG. 1A. Although it is preferred that transceivers 45, 46 be mounted on a collar which is stabilized, such transceivers 45, 46 may of course be mounted on a cylindrical collar which does not have stabilizing fins.

Electronic circuits and microprocessors, memories, etc. used to control transceivers 45, 46, receive data from them, and process and store such data are mounted on a sleeve 21 which is secured within collar 20 or 20'. Such sleeve has a path 40' by which drilling mud may pass through the interior of drill string 6 to the interior of bit 30.

The tools (collars) 20 or 20' including transceivers 45 and 46 and the electrical apparatus mounted on sleeve 21 are especially adapted to measure borehole diameter and to measure characteristics of the mud which returns upwardly in annulus 10 after it passes through bit 30. Such mud usually has entrained cuttings, rock chips and the like and may have gas bubbles 19 entering the annulus mud from an earth formation. It is the fact of the occurrence of this gas influx or "kick" and the time that it occurs as the borehole is being drilled that is important to the driller. As explained below, the apparatus and methods of this invention measure characteristics of the returning mud, such as sonic impedance and sonic attenuation, to determine if and when a gas influx has occurred.

Description of Ultra-sonic Transceivers and Placement on Collar

1) Ultra-sonic sensor construction in general

Figure 2A:
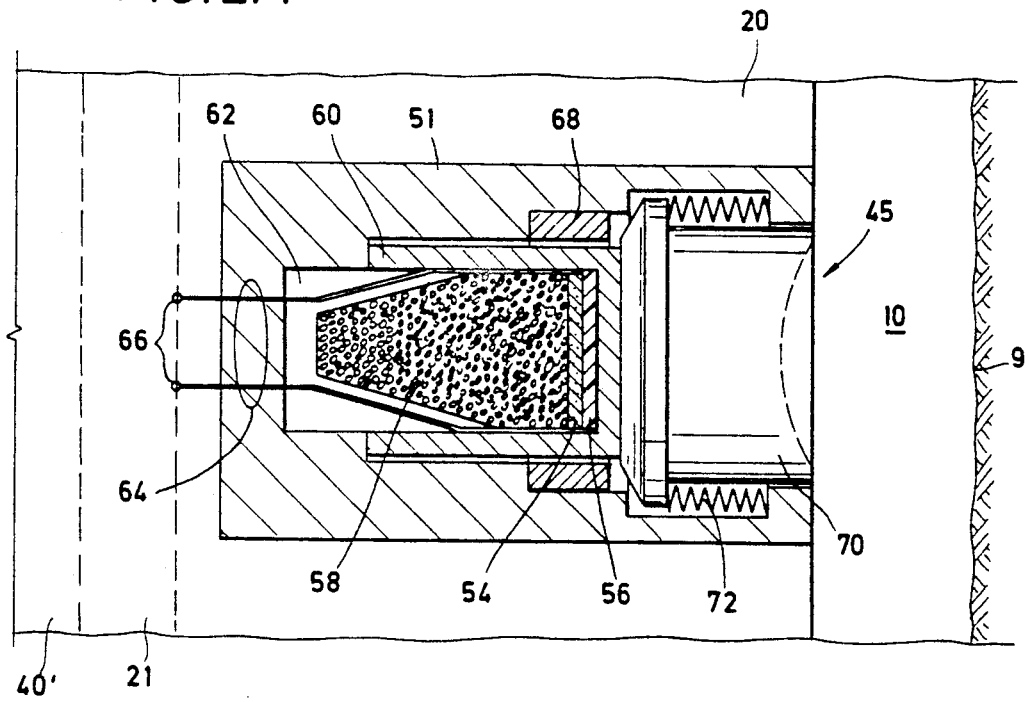
FIG. 2A illustrates in schematic form the ultra-sonic sensor assembly of the invention.

FIGS. 1, 1A and 2A illustrate schematically the ultra-sonic transceivers 45, 46 of the invention. Such transceivers are secured in the collar 20 or 20' to face the annulus 10 of the borehole 9. FIG. 2A shows that the transceiver is disposed in a steel cup 51 secured within a cavity of the cylindrical wall 23 of collar 20' or stabilizer fin 27 of collar 20. Alternatively, the transceiver could be installed directly into a cavity of the collar 20.

The sensor of the transceiver 45 is a piezo-electric disk 54 which is preferably a flat circular slice of ceramic material. Disk 54 is mounted between one (or more) impedance matching layer 56 and a suitable absorbing or backing element 58. The matching layer 56 is fabricated of a low density material such as magnesium or hard plastic. The backing element 58 includes high impedance grains (typically tungsten or lead balls) molded in low impedance material (such as epoxy or rubber).

These three elements, the ceramic disk 54, matching layer 56 and backing element 54 are hereinafter referred to as the sensor stack. They cooperate to generate or emit an ultra-sonic pulse outwardly toward the wall of borehole 9 through drilling mud of annulus 10 and to receive sonic echo pulses which are reflected back to ceramic disk or sensor 54.

The sensor stack is encapsulated in a rubber jacket 60 which isolates the sensor stack from high pressure drilling fluid in annulus 10. Such fluid isolation avoids electrical shorting and corrosion of the sensor stack elements and provides electrical insulation of electrodes, leads, and connections to sensor disk 54.

The space 62 between the jacket 60, backing material 58, and cup 51 is filled with a highly deformable material such as rubber. Such rubber and the rubber jacket 60 cooperate to surround the sensor stack with rubber in order to dampen noise transmitted in the collar 20 from the drilling process, and partially to absorb high shock forces on the sensor stack created during a typical downhole drilling operation. The rubber in space 62 also functions to allow the sensor stack to move or deform under pressure or due to thermal expansion.

Electrical leads 64 are connected between outer and inner surfaces of sensor 54 and terminals 66 of electronics module 22. Such leads 64 run through the rubber 62 and through the cup 51 as will be explained in greater detail below.

Additional noise filtering is preferably provided by a ring 68 of low impedance material placed about the rubber jacket 60 in longitudinal alignment with sensor disk 54. Ring 68, which is made of materials such as epoxy, rubber, plastic and the like, (or even grease or mud) reduces the level of high frequency noise transmitted through the steel collar 20 that reaches the disk 54. Ring 68 reflects noise transmitted through the drill string and collar which could reach ceramic disk 54. It acts as a mechanical high frequency noise insulator or filter so as to increase the signal to noise performance of the transceiver 45. A high signal to noise ratio is important under drilling conditions where high speed mud flowing in path 40' of the collar 20 might generate noise in the frequency range of the transceiver measurement.

A delay-line 70 is placed outwardly of sensor disk 54. Such delay-line 70 provides mechanical protection to the sensor stack as well as providing an important role in the measurement of drilling fluid sonic impedance. Measurement of drilling fluid sonic impedance provides one means for gas influx detection. The delay-line 70 also facilitates short stand off detection of the borehole as explained below.

The delay-line 70 is fabricated of low sonic impedance materials such as plastic, epoxy or rubber. It distributes impact forces on its outer face over a relatively wide area inwardly toward the matching layer 56. The delay-line 70, rubber jacket 60 and matching layer 56 cooperate to broadly distribute such impact forces to the ceramic disk 54, which is fabricated of an inherently brittle material. Furthermore, delay line 70 is mounted with respect to cup 51 so as to isolate the sensor stack from further torque caused by the outer face of the delay-line 70 and collar 20 rubbing against the borehole when the drill string is turning in the borehole 9. The delay-line also protects the rubber jacket 60 from damage due to banging and scraping of the tool 20 against the wall of borehole 9.

The delay-line 70 is spring mounted within cup 51 by springs 72 which maintain contact between delay-line 70 and rubber jacket 60 even if the sensor stack moves outwardly or inwardly due to expansion or contraction with temperature and pressure variations.

In summary, FIG. 2A illustrates that the ceramic sensor 54 is protected both acoustically and structurally. Structural protection of sensor disk 54 is provided by its shock mounting: longitudinally by the steel cup 51 and the tightly fitting rubber jacket 60; inwardly by the soft rubber filling 62; and outwardly by the delay-line 70 and its spring 72 mounting with respect to cup 51. Such spring mounting allows expansion and compression of the backing element 58 under pressure and temperature changes toward the outward face of transceiver 45. Rubber sleeve 60 serves to isolate the sensor stack from pressurized fluid and to allow its outer face to move inwardly and outwardly, while maintaining contact with delay-line 70.

2) Ultra-sonic sensor preferred construction

Figure 2B:
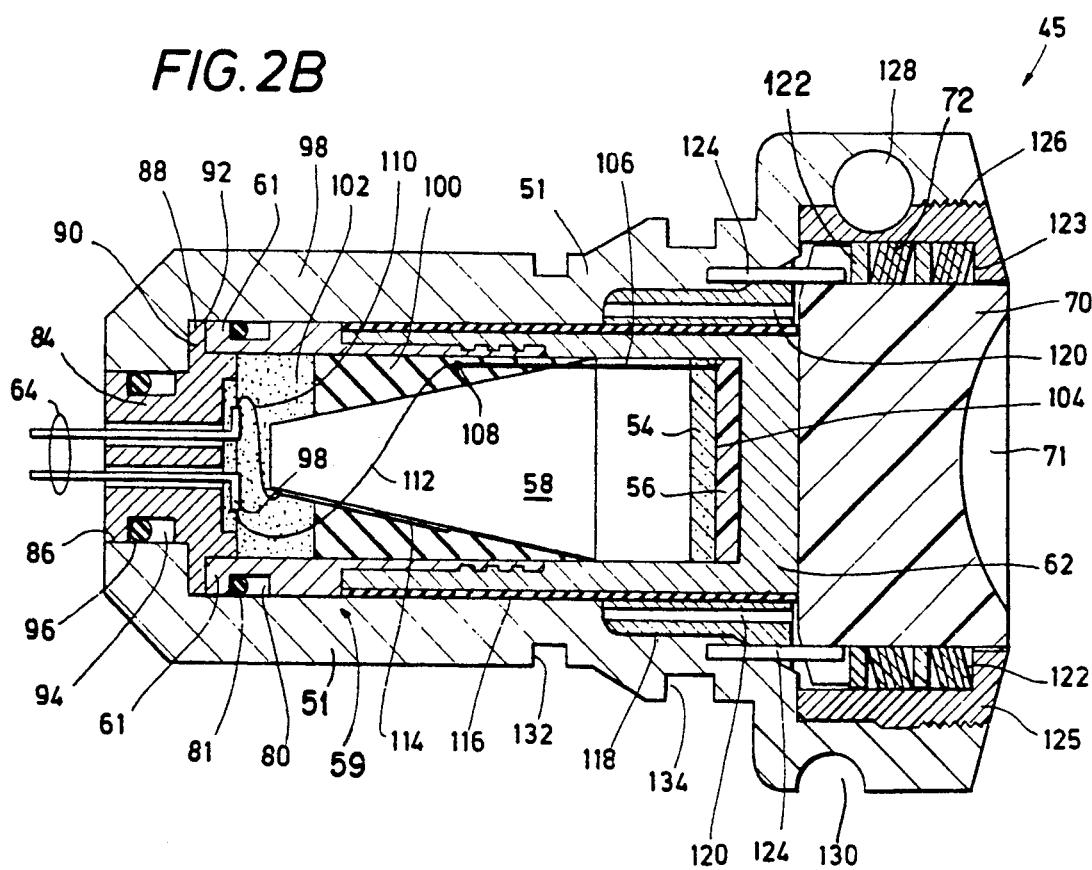
FIG. 2B illustrates a preferred embodiment of the sensor assembly of the invention.

FIG. 2B illustrates a preferred construction of the transceiver sensor assembly 45 of the invention. The sensor stack comprising ceramic disk 54, matching layer 56 and backing element 58 are mounted within metallic cup 51.

The ceramic disk 54 is fabricated of material characterized by low sonic impedance and high internal damping. Lead metamobate ceramic polarized over its entire surface is preferred. When an electrical voltage is applied across its outer and inner flat surfaces, the thickness of the ceramic disk changes slightly. When the impressed voltage is removed, the ceramic disk returns to its original thickness. If the ceramic disk has an oscillating voltage of a certain time length, here called a pulse, the ceramic disk oscillates. An acoustic pulse is emitted from the disk because of the oscillating thickness of the ceramic disk changes in response to the oscillating voltage.

With no voltage impressed on the disk, it serves as a receiver. When an acoustic wave or oscillating pulse is applied to the face of the disk, an electrical oscillating signal between the two faces of the disk is generated.

In a pulse-echo sensor or transceiver, i.e., the ceramic disk 54 of the transceiver 45 of this invention, the same ceramic disk is used to emit an acoustic pulse and receive an echo of the emitted pulse and produce an electrical signal in response thereto.

The oscillations of the ceramic disk 54 during the emitting phase are preferably damped before the disk is used to receive a returning echo acoustic wave. Such damping must be effective because the returning echo pulses are relatively small in amplitude. In other words, sensor ringing noise after the emitting phase should be kept to a minimum.

Decay control of the emitting oscillation is a primary function of backing element 58. It should be in contact with ceramic disk 54 as shown in FIG. 2B. Backing element 58 drains the acoustic energy out of the ceramic disk 54 after an emitting voltage pulse is applied thereto. Backing element 58 absorbs and dissipates such energy so that it will not bounce backwards toward the ceramic disk 54 to generate a noise signal after the emitting phase is over.

Specifically, the backing element 58 preferably has a sonic impedance approximately the same as the material of the ceramic disk 54. Accordingly, little acoustic energy is reflected back toward the ceramic disk 54 as it meets the interface between ceramic disk 54 and backing element 58. On the other hand, the backing element 58 should have high sonic attenuation so that energy into the backing is quickly attenuated as it travels backward into the backing element and bounces from its extremities. It is important that the backing element be fabricated of a material which maintains its properties of high acoustic attenuation and ceramic matching . impedance under conditions of high pressure and high temperature.

The preferred raw material for backing element 58 includes unvulcanized rubber stock, rubber compounding chemicals and vulcanizing agents, and tungsten powder. A roll mill is used to mix the compounding chemicals and vulcanizing agents into the rubber stock, and for the subsequent mixing of tungsten powder into the compounded stock. Once the tungsten and rubber have been thoroughly blended, the resulting material is removed from the mill and compression molded in a heated platen press to form and vulcanize the finished composite.

The preferred rubber stocks are synthetic isobutylene-isoprene elastomers. The tungsten powder should be of small grain size. The compounding chemicals and vulcanizing agents include small amounts of ZnO powder, Stearic Acid and Resin SP. The elastomer, tungsten powder, compounding chemicals and vulcanizing agents may be selected in proportion and grain size and mixed and processed according to well known techniques of powder metallurgy to form a backing element with the properties identified above.

The matching layer 56 is preferably fabricated of a thin layer of 30% carbon-filled PEEK. PEEK is a hard plastic having a chemical name polyetheretherketone. The optimum impedance of matching layer 56 is selected such that it is substantially equal to the square root of the impedance of the ceramic disk 54 multiplied by the impedance of rubber layer 60.

Virgin PEEK hard plastic is preferred as the material for delay-line 70. Epoxy or phenolic may be substitute materials for delay-line 70. The sonic impedance of PEEK provides excellent sonic coupling with heavy drilling mud. Its sonic attenuation is low and has good mechanical and chemical properties for downhole application.

A concave outwardly facing depression 71 of the outer face of delay-line 70 is preferably provided in transceiver 45. Such depression 71 provides a small amount of focalization of the sonic energy emitted and received via the delay line 70. Such focalization improves the reflection of borehole echoes where rugose walls are encountered.

Such depression 71 also provides separation between the outer face of the transceiver 45 and the borehole wall when the collar 20 is not separated from the borehole wall. With such "zero stand-off" condition, returning echoes from the outer face of the delay line 70 may be separated from zero stand-off formation (borehole wall) echoes.

The depth of the depression 71 in the outer face of delay-line 70 is preferably small so as to avoid the possibility that mud cake of drilling cuttings, sticking shales, and mud particulates do not accumulate there. Excessive concentration of mud cake in the path of the sonic pulse excessively attenuates a returning borehole echo.

An isolation jacket 59 isolates the sensor stack elements 58, 54 and 56 from water entry via the steel cup 51. The isolation jacket 59 includes a steel sleeve inner part 61 and a rubber jacket outer part 60. The outer part 60, preferably of viton type rubber, is molded onto the steel sleeve 61. A groove 80 in the inner steel sleeve 61 has an O-ring 81 placed in it which provides borehole fluid isolation via the cup 51 to the sensor stack.

Fluid isolation is also provided by means of the viton jacket outer part 60, but drilling fluid pressure is applied about the jacket 60 which separates the sensor stack from the drilling mud. Thus, although isolated from fluid, the sensor stack is under the same pressure as the drilling mud.

An electrical feed-through element 84 is provided in an inner hole 86 of the cup 51. A flange 88 of feed-through element 84 is disposed between shoulder 90 of cup 51 and a bottom annular end 92 of steel sleeve inner part 61 of the isolation jacket. Groove 94 of feed-through element 84 has an O-ring 96 placed in it to provide back-up fluid isolation of the electronic modules 22 from inside the cup 51. Electrical pins 64 run from an inner position of cup 51 through feed through 84 and terminate at feet 98.

A thin aluminum sheet 104 is secured in contact with the outer face of ceramic disk 54 by means of an epoxy glue. A strip of aluminum 106 extends from the sheet 104 inwardly to a terminal point 108 inwardly of the frusto-conical surface of the backing element 58. A conductive wire 112 is attached between one of the feet 98 of the electrical pins 64 and the terminal point 108. A conductive wire 110 is secured between the other of the feet 98 of the electrical pins 64 and a sheet of brass 114 which covers almost the entire conical surface of backing element 58.

The brass electrode 114 includes several folds and kinks (not illustrated) to allow thermal expansion of the backing. It is secured to the backing element 58 by means of an epoxy glue. Such glue is non-conductive, but enough contact is provided such that electrical contact is made between the brass sheet and the tungsten grains of the backing material to establish electrical conductivity between wire 110, brass sheet electrode 114, backing material 58, and the inner face of ceramic disk 54.

Connection to the backing element 58 by means of sheet electrode 114 is advantageous because it avoids providing a third electrode between the inner face of the ceramic disk 54 and backing element 58 which could decrease the damping function of the backing. Also the wire 110 is not subjected to extreme thermal expansion because it is connected near the inner tip of the conical portion of backing element 58.

The space between the interior of isolation jacket 59, backing element 58, and feed through element 84 is filled outwardly with RTV silicon rubber 100 and inwardly with epoxy 102. The RTV rubber 100 allows the wire 112, which runs from a foot 98 of pins 64 to terminal 108 of aluminum 106, to move outwardly or inwardly with movement of sensor stack 58, 54, 56. Wire 112 is looped within rubber 100 allowing it to move radially with radial movement of the sensor stack. In order to limit large thermal expansion however, the volume of RTV rubber 100 filling is limited because of the large thermal expansion of RTV rubber at high temperature. Accordingly, the inner space is filled with epoxy 102.

Filling such inner space 102 with epoxy is advantageous because the thermal expansion of epoxy is smaller than that of RTV rubber. The epoxy 102 also serves to centralize and secure the tip of the conical section of backing element 58 and to prevent the ceramic disk 54 from being displaced inwardly in cup 51 with multiple heat or pressure cycles. Such epoxy 102 also serves to close the inner side of the sensor stack via spaces from inside the transceiver 45.

A thin tube 116 of nitrile rubber is placed about the cylindrical sides of the rubber jacket outer part 60. Such tube provides a sliding surface of contact for rubber jacket outer part 60 when such rubber jacket moves outwardly or inwardly with changes of temperature. The tube 116 also limits inward displacement of delay-line 70 if a shock force is applied to the outer face of delay-line 70. Accordingly, the tube 116 provides limited shock absorbing protection of ceramic disk 54 when the transceiver 45 is in service while drilling a borehole.

A ring 118 is placed about jacket 60 and tube 116 in the vicinity of ceramic disk 54. It is constructed of low sonic impedance material in order to improve acoustic reflection and thus isolation of the disk 54 against drilling and pumping or high speed fluid flow noise transmitted through steel drilling pipe 6, collar 20 and bit 30. Holes 120 in filler ring 118 provide a space to relieve pressure in the annulus between tube 116 and cup 51.

Wave springs 72 act between flanges 122 of delay-line 70 and shoulder 123 of window nut 125 to force delay-line 70 inwardly against the outer annular edge of tube 116 and the outer surface of jacket 62. Window nut 125 is secured within cup 51 by threads 126. Thus, the springs 72 serve not only to force window 70 properly adjacent jacket 62, matching layer 56 and ceramic disk 54, it also serves to protect ceramic disk 54 from shock impacts against the outer face of delay-line 70. Such shock impacts are also partially absorbed by the tube 116, jacket 62, backing element 58 and RTV rubber filler 100.

Pins 124 placed in mating holes of cup 51 and delay-line 70 prevent rotation of delay-line 70 with respect to the sensor stack. Accordingly, friction forces on delay-line 70 from contact with borehole wall 9 during tool rotation are not transferred to the sensor stack.

The cup 51 includes two holes 128, 130 which are perpendicular to the axis of the sensor 45. When a pin is inserted in hole 128, for example, the window nut 125 is locked in rotation. When a pin is inserted in hole 130, cup 51 is looked in rotation, which allows window nut 125 to be removed when needed. O-ring grooves 132, 134 in which O-rings are placed when cup 51 is placed in a cavity of collar 20 provides isolation of the interior of collar 20 from drilling fluid in the annulus 10.

In order to improve the accuracy of the caliper or borehole diameter measurement, and to broaden the hole size range detectable with the transceiver 45 of this invention, the transceiver 45 of FIGS. 2A and 2B is preferably mounted near or on the stabilizer blades 27 of the collar 20 as illustrated in FIGS. 1 and 1A. The accuracy of the ultra-sonic measurement is enhanced for several reasons.

First, where the transceiver is mounted on a stabilizer fin, there is less mud through which an emitted pulse must travel from the sensor to the borehole wall and back. Second, there is less eccentricity or canting of the tool 20 in the borehole 9 in the vicinity of the stabilizer blades, so that the standoff distance s measured by two diametrically opposed transceivers result in a better measure of a diameter of the borehole. Ideally borehole diameter should be measured perpendicularly to the borehole walls.

Third, with a shorter distance between the sensor and borehole wall, there is less spreading of the sonic beam resulting in greater signal reflection back to the transceiver from the borehole wall. Fourth, with shorter standoff distances, especially where transceivers 45, 46 are mounted on stabilizer blades, higher sonic frequencies may be used thereby improving the accuracy of detection of the first borehole echo. Finally, but importantly, the measurement of the diameter of the borehole should be accomplished with the tool centered in the borehole so that the actual diameter of the borehole is measured rather than a chord of such borehole. Providing the transceiver on a stabilizer fin of a collar or on a collar having stabilizer fins centers the collar in the borehole and as a result, the standoff measurement with the transceiver and associated electronic is more accurate.

3) Electronic Module

Figure 3A:
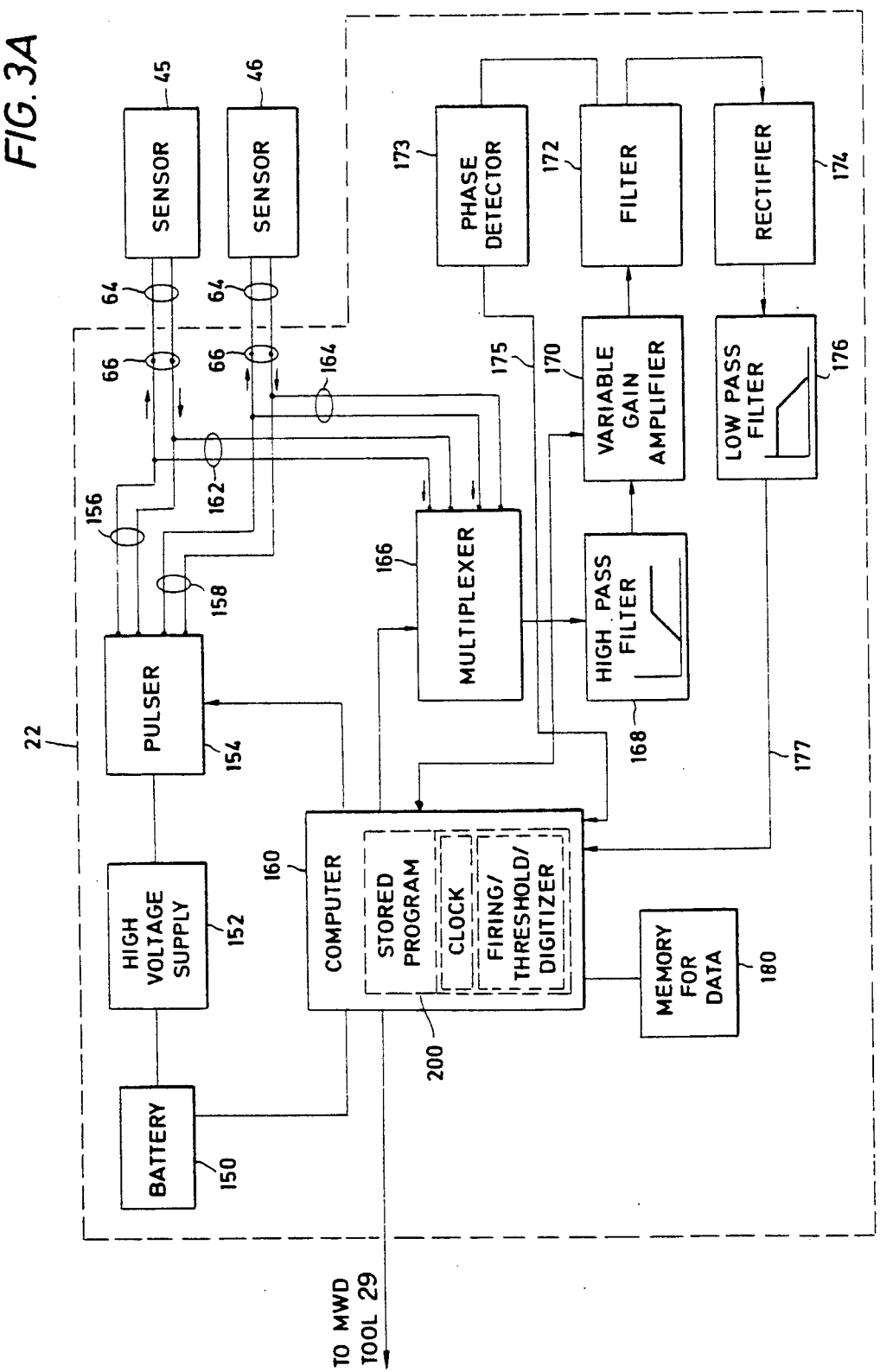
FIG. 3A illustrates in block diagram form the circuits, computer and stored program of a tool electronics module which controls the firing of a source pulse transmitter and the echo signal reception of one or more sensors and which processes echo data to generate signals representative of borehole diameter, mud impedance and mud attenuation.

The electronic module 22 of collar 20 is illustrated in FIG. 3A. Such module is connected to terminals 66 which are connected to sensors 45 and 46 mounted on collar 20 as discussed above. A downhole battery 150 is preferably provided in module 22 as a d.c. power source. Other sources of electrical power are of course known in the art of downhole tool design. High voltage supply 152 steps up the d.c. voltage to power pulser 154 which generates a high frequency oscillation at a preferred frequency of about 670 KHz. Computer 160 and pulser 154 direct short bursts of these high frequency voltage oscillations first to leads 156 for application to sensor 45, and after a receive time for sensor 45 has passed, then to leads 158 for application to sensor 46. Of course, one sensor only may be used, or more than two, but two diametrically opposed sensors are preferred for the measurements described below.

The received voltage pulses, or return echoes, are sensed on leads 64 of sensor 45 and 46 following each burst of sonic pulses. Such voltages are applied via lead pairs 162, 164 to multiplexer 166. Multiplexer 166 in turn, under control from computer 160, passes the return echo voltages first to high pass filter 168 where low frequencies in the return voltage pulses are removed.

A variable gain amplifier 170 amplifies the return signal which is then filtered, rectified and low pass filtered by circuits 172, 174, and 176 respectively. The gain of amplifier 170 is increased when computer 160 detects low amplitude return echoes. The output of low-pass filter 176 is an envelope of high frequency voltage return echoes generated by sensors 45 and 46 in sequence. In the preferred embodiment of the apparatus of this invention, digitization of envelope signals on lead 177 is accomplished by a signal processing and sensor firing protocol of computer 200. The envelope signal on lead 177 is digitized in this manner, rather than with a conventional A/D converter circuit in order to conserve scarce electrical power for a down hole measurement during long time periods of drilling.

The digitizing software and firing pattern provides digitization of the envelope signal on lead 177 by firing a given sensor (that is, sensor 45 or 46) N times where N is preferably between 5 and 15. Each firing is performed with a smaller threshold (or higher gain). For each gain/threshold combination, a proper delay is set to avoid noise detection.

FIG. 3B illustrates a firing/echo pattern which is repeated eight times. Eight counters are provided, each associated with one of the eight threshold levels. Each counter records the time of a crossing of its threshold. When a set time is reached (for example 200 microseconds), the processor records the number of threshold crossings of the envelope signal on lead 177 associated with each counter. In FIG. 3B, the dots on the signal envelope represent the position of signal detection. The formation echo amplitude of crossing C13 is between threshold (1) and (2). Its peak amplitude is at the time associated with crossing C13. It can be seen that the envelope signal on lead 177 is digitized by the multiple firing-multiple threshold technique with multiple counter software procedure described above.

After digitization, such envelope signals of the echo signals are processed in computer 160 according to the methods discussed below. Signals representative of the processing of the envelopes of the returning signals are stored in module memory 180 or are passed along to MWD tool 29 for transmission to the surface instrumentation 7 for further processing.

Delay-line and Borehole Echo Determination

Figure 4:
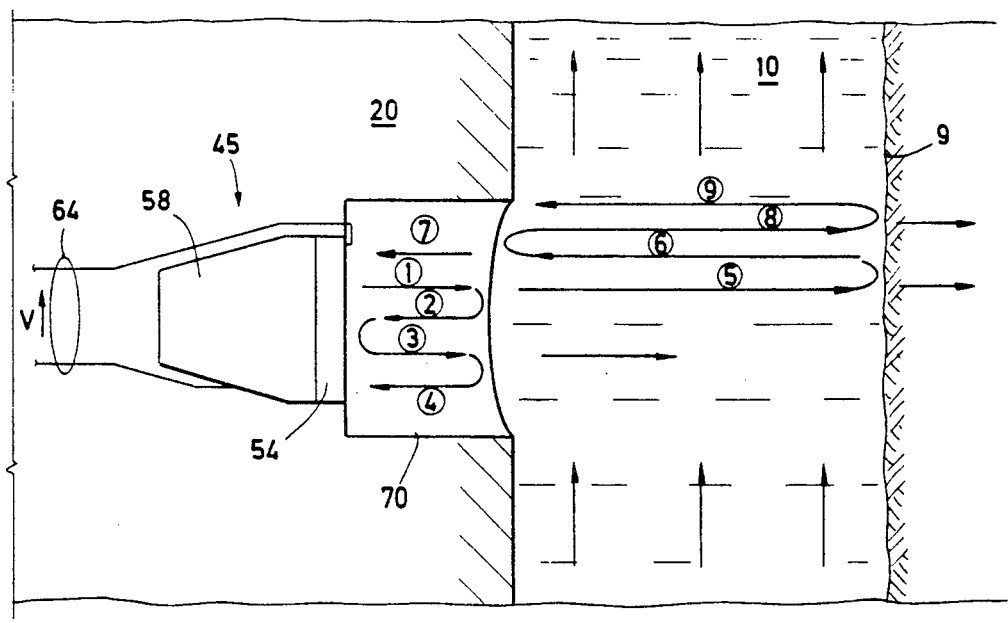
FIG. 4 is a schematic diagram illustrating ultra-sonic pulse generation by the ceramic disk of the sensor stack and the echoes from the interface of the delay-line with the drilling fluid and the echoes from the formation or borehole wall.
Figure 5:
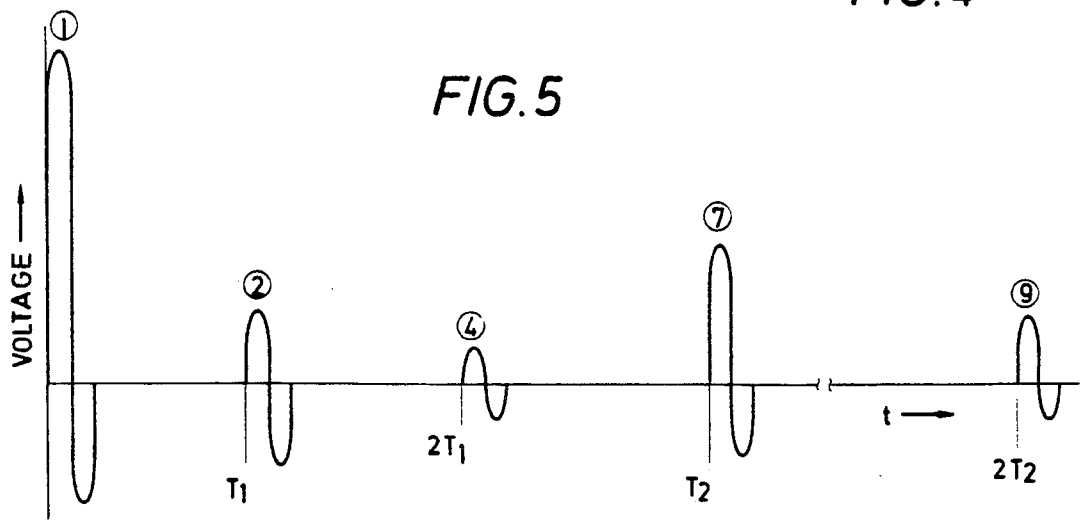
FIG. 5 is a voltage versus time illustration of the ultra-sonic pulse emitted into the drilling fluid toward the borehole wall and various return echo pulses from the interface of the delay-line and the drilling fluid and from the borehole wall.
Figure 6A:
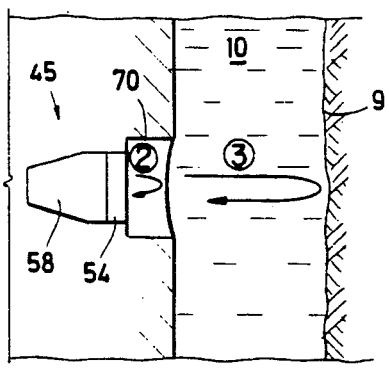
FIGS. 6A and 6B illustrate schematically and by a voltage versus time graph of the relative amplitude and time spacing of an emitted ultra-sonic pulse and its return echo, first from the interface between the delay-line of the sensor stack and drilling fluid of the borehole, and second from the borehole wall.
Figure 6B:
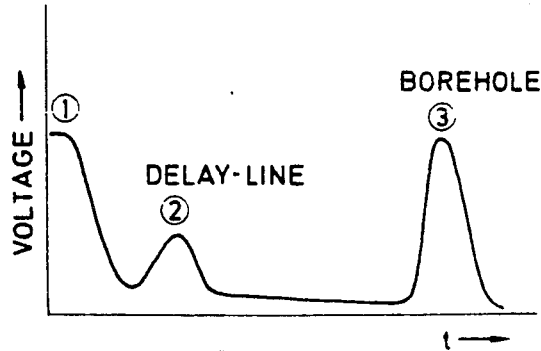

The measurement of standoff and borehole diameter is illustrated schematically in FIGS. 4 and 5 where transceiver 45 includes backing element 58, ceramic disk 54, and delay-line 70. A voltage pulse V of high frequency oscillation is impressed on ceramic disk 54 which responds by emitting high frequency acoustic pulses, depicted as arrow (1) into delay-line 70. Return echoes are sensed by ceramic disk 54 and a voltage representative thereof is impressed on leads 64. Only one timing cycle for a transceiver is depicted in the illustration.

When the sonic pulse (1) reaches the interface between the delay-line 70 and the drilling fluid in annulus 10, part of the sonic pulse is transmitted through the interface and into the annulus as depicted by arrow (5). Part of the sonic pulse is reflected back toward the ceramic disk 54 as depicted by arrow (2). The amplitude of the reflected signal (2) depends on the difference between the sonic impedance of the drilling fluid and the sonic impedance of the delay-line 70.

The reflected sonic pulse or "echo" (2) strikes the ceramic disk 54, and excites it. Such mechanical excitation generates an electrical signal representative of the amplitude and time delay of the sonic echo. The signal is amplified by the electronic module 22 and applied to the downhole computer 160 as described above. A first delay-line echo is detected as the pulse (2) of FIG. 5 occurring at time T1 after the emitted sonic pulse depicted as pulse (1).

Sound waves in delay line 70 bounce back and forth between the ceramic disk 54 and the drilling fluid of annulus 10. At each reflection, the amplitude of the sound wave pulse is reduced because part of the energy is transmitted through the interface and of course is lost as energy of a reflected pulse. Such echoes bouncing back and forth are depicted as waves (3) and (4) of FIG. 4. Sonic pulse echo (4) is detected at the amplifier 170 and computer 160 at time 2T1.

A portion of pulse (1) is transmitted into the drilling fluid of annulus 10 as depicted by arrow (5). Pulse (5) bounces or is reflected from the formation 9 interface, and an acoustic pulse echo (6) travels towards the delay-line 70. Part of the energy of echo pulse (5) is transmitted into the formation.

Echo pulse signal (6) reaches the delay-line 70 where part of its energy is transmitted into the delay-line as pulse (7). This pulse travels through delay line 70 and excites ceramic disk 54. Such excitation is detected as the amplifier 170 or computer 160 output (7) at time T2 in FIG. 5.

Multiple echoes can be detected, especially in light drilling fluid where sonic attenuation is small. An example of a multiple echo is shown by the sonic pulses as depicted by arrows (8) and (9). FIG. 5 illustrates multiple echo detection of delay-line echoes of pulses (2) and (4) and of borehole echoes of pulses (7) and (9).

As illustrated in FIG. 1, gas influx bubbles 19 may enter the drilling fluid in the annulus 10 from formation layers through which the bit is drilling. Such bubbles flow upwardly by and pass in front of the transceivers 45, 46. The sonic attenuation and impedance of the drilling fluid are changed by the gas. The signal processing of the electronic module 22 of FIG. 3A detects such changes in the characteristics of the drilling fluid.

FIGS. 6A, 6B to 9A, 9B illustrate several categories of return echo patterns which are the result of the measurement apparatus configuration, borehole geometry, cuttings, and gas bubbles in the drilling fluid. FIGS. 6A, 6B, to 9A and 9B illustrate conditions of clean mud, cuttings in mud, a small amount of gas in the mud, and a great amount of gas in the mud, respectively. The FIGS. 6B, 7B, 8B, 9B illustrate the kinds of echo signal returns which are to be expected from the conditions of FIG. 6A, 7A, 8A, 9A. The "B" diagrams of the Figures represent the envelope of the voltage output of the amplifier 170 after rectification of the return pulse by rectifier 174 of FIG. 3A. Such "B" diagrams are plots of voltage amplitude versus time. The time reference is from the excitation pulse (1) which is shown as saturation of the amplifier 170. Such excitation pulse (1) is masked in the digitization method as described above in connection with FIG. 3B.

After firing of the excitation pulse represented as pulse (1), an echo from the front face interface between delay-line 70 and drilling fluid in annulus 10 is returned to the ceramic disk 54 as pulse (2). At a later time the formation echo is returned to ceramic disk 54 as indicated by pulse (3). The excitation voltage applied to ceramic disk 54 is maintained at a constant level. Accordingly, the echo amplitudes result from a constant amplitude emitted pulse.

The amplitude of the delay-line echo (2) depends secondarily on the attenuation in the matching layers 56 and rubber layer 60 (of FIGS. 2A, 2B, but not illustrated in FIGS. 4, et seg.) and the delay-line 70. Typically, the attenuation of the matching layer varies slightly with temperature. But the amplitude of the delay-line echo (2) depends primarily on the coupling with the drilling fluid, because the reflection coefficient at the delay-line - drilling fluid interface is related to the sonic impedance of the fluid. In other words, $$R_{DL} = \frac{Z_{MUD} - Z_{DL}}{Z_{MUD} + Z_{DL}}$$

where $R_{DL}$ is the reflection coefficient, $Z_{MUD}$ is the sonic impedance of the drilling fluid, and $Z_{DL}$ is the sonic impedance of the delay-line.

The borehole echo amplitude (that is, the echo from the formation wall of the borehole) depends on several parameters. One such parameter is the sonic attenuation of the drilling fluid. Sonic attenuation of the drilling fluid increases nearly linearly with mud density for a given frequency. Due to this effect, the formation echo pulse (3) of FIG. 6B may vary by a factor of 100, with varying standoff distances and mud attenuation.

Another such parameter is the reflectivity $R_f$ of formation wall. Such wall reflectivity depends on the sonic impedance of the formation $Z_f$ and the rugosity of the formation. Variation in borehole wall reflectivity can affect the amplitude of the borehole echo pulse by a factor of 10.

Another parameter affecting the amplitude of the borehole echo pulse is the degree of parallelism between the sensor face and the borehole wall. The amplitude may vary by a factor of 10 due to such parallelism factor. In other words, the strongest borehole signal, other factors being equal, results from the transceiver being perpendicular to the borehole wall.

Other factors affecting the amplitude of the borehole echo include the delay-line sonic attenuation and the coupling between the drilling fluid and the delay-line. Such coupling varies with the density of the drilling fluid (typically it improves with increasing density) because the mud sonic impedance depends on the mud density. Each of the factors of delay-line attenuation and mud delay-line coupling may affect the amplitude of the borehole echo by a factor of two.

Figure 7A:
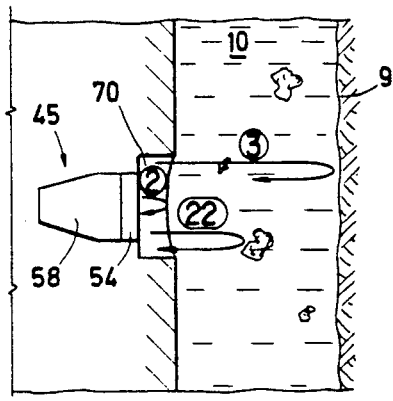
FIGS. 7A and 7B illustrate schematically, and by a voltage versus time graph, the relative amplitude and time spacing of an emitted ultra-sonic pulse and return echoes from the delay-line-drilling fluid interface, from the borehole wall, and from cuttings in the drilling fluid.
Figure 7B:
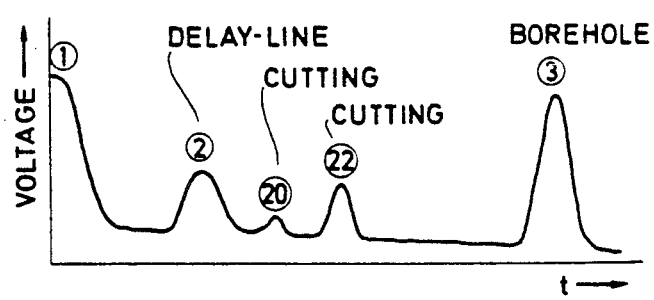

FIG. 7A depicts the situation and effects of drilling cuttings being present in the drilling fluid. Each cutting reflects part of the emitted sonic pulse back toward the ceramic disk 54. As a result, each cutting generates a signal at the output of the amplifier. Such cutting echoes are depicted as echoes (20), (22) in FIG. 7B. Their amplitude depends primarily on the size of the cutting and the sonic attenuation in the mud. With low sonic attenuation mud, most cuttings typically have signals which are smaller or equal to the borehole pulse (3). With high sonic attenuation mud, the borehole echo (3) is attenuated by a larger ratio than the cutting echoes (20), (22) because it is always more distant from the disk 54. In such a case, the borehole echo (3) may become smaller than the cutting echoes, (20), (22).

Figure 8A:
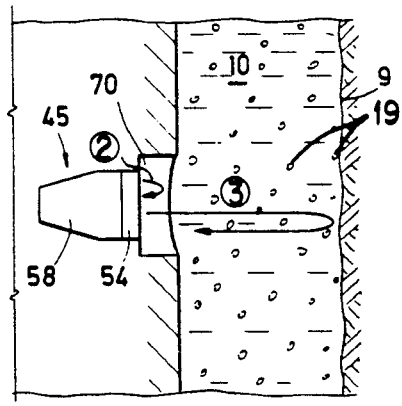
FIGS. 8A and 8B are illustrations similar to those of FIGS. 5A, 5B and 6A, 6B illustrating small gas concentration in the drilling fluid resulting in a drilling fluid sonic attenuation increase which reduces borehole echo amplitude.
Figure 8B:
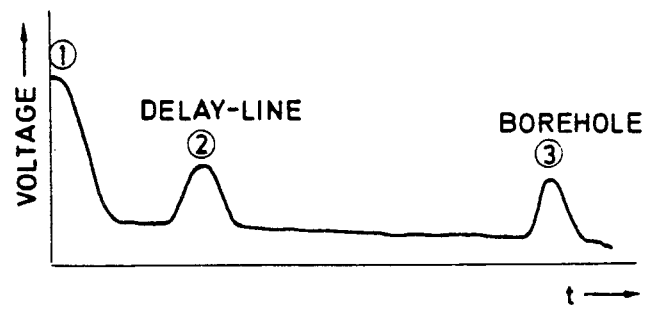

FIG. 8A depicts the situation and effects of a small amount of gas in the mud, which typically is in the form of small gas bubbles 19. For such a condition the sonic attenuation of the mud increases. As a result, the amplitude of borehole echo (3) is reduced as illustrated in FIG. 8B. The delay-line echo (2) varies slightly, because the mud impedance decreases slightly with a small increase in gas concentration. Because the delay-line impedance is normally higher than the mud impedance, the delay-line echo (2) increases slightly with a small increase in gas concentrated in the mud.

Figure 9A:
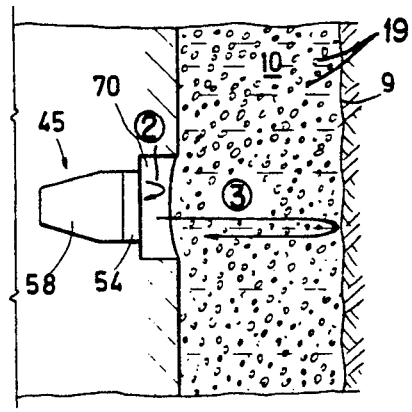
FIGS. 9A and 9B are illustrations similar to those of FIGS. 7A and 7B but for the case of high concentration of small gas bubbles in the drilling fluid, resulting in almost complete attenuation of the borehole echo, but also resulting in an increase in the amplitude of the delay-line/drilling fluid echo due to a change in the sonic impedance.

FIG. 9A depicts the case of a large gas concentration of small bubbles due to a gas influx into the drilling mud in annulus 10. Large gas concentrations typically are defined as gas fractions equal to or above 1% of the mud fraction. For such a gas concentration, sonic mud attenuation may reach 15 db/cm, so that the borehole echo signal (3) is greatly attenuated. Such small amplitude of borehole echo (3) may make its detection difficult. The delay-line echo pulse (2) amplitude increases up to 10% with the gas concentration in mud.

Figure 9B:
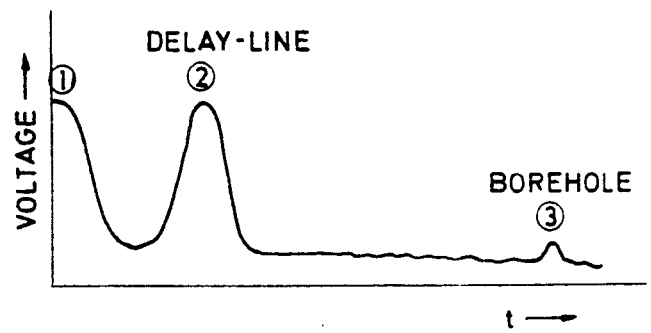

FIGS. 9C and 9D are similar to FIGS. 9A and 9B, but represent the case of large gas bubbles in annulus 10 passing sensor 45 on their way to the upper surface of the borehole. Such large bubbles may produce an echo as at (4) of FIG. 9D which is of the same relative absolute amplitude as that of the delay-line echo (2). It has been found that the phase of a large bubble echo (4) is reversed or 180° out of phase from the phase of other echoes. In other words the signal (4) of FIG. 9D is a rectified envelope of a high frequency pulse which is 180° out of phase with other echo pulses. Phase detector 173 detects such phase shift of the oscillation signal of the returning echoes and sends a signal to computer 160 when such a condition is sensed.

The fact of the 180° phase shift of an echo pulse provides a means for identifying large gas bubble; that is, the phase of each echo is first determined. If such phase is 180° from that of the delay-line echo, such echo represents a large gas bubble. For such a case, a signal is sent to the surface instrumentation under control of computer 160 via MWD sub 29 so that an alarm may be generated to alert the driller as to the fact of a large gas bubble migrating to the surface which has been detected near the bottom of the borehole.

The stored program 200 of computer 160 has stored therein echo determination logic for distinguishing borehole echoes and delay-line echoes from cutting echoes and other spurious echo signals. Such logic is in part based on the following considerations.

The formation or borehole wall is the most distant reflector. Cuttings are always closer to the ceramic disk 54 than is the borehole wall. Disregarding the case of double echoes, the borehole echo should always be the last echo.

In most drilling conditions cuttings will always be present in the path of the sonic beam. The larger the size of the cuttings, the fewer individual cuttings echoes will be present.

In a drilling fluid of low attenuation, most cuttings produce an echo smaller than the formation.

In a drilling fluid of high attenuation, it is possible that the cutting echo signal may be larger than the formation echo signal if the difference in sonic path length is relatively great.

After the arrival of an echo at the sensor, the sensor noise is increased by the noise of this echo. Such noise decays to the level of sensor noise.

Small cuttings (those of less than 1 MM diameter) create an increase of base line noise, but usually cannot be individually recognized.

Figure 10:
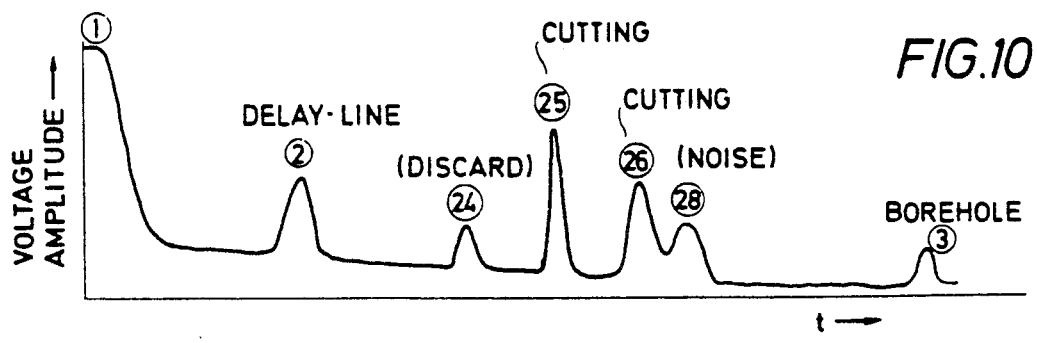
FIG. 10 illustrates echoes which are sensed due to drilling cuttings entrained in the drilling fluid.
Figure 11:
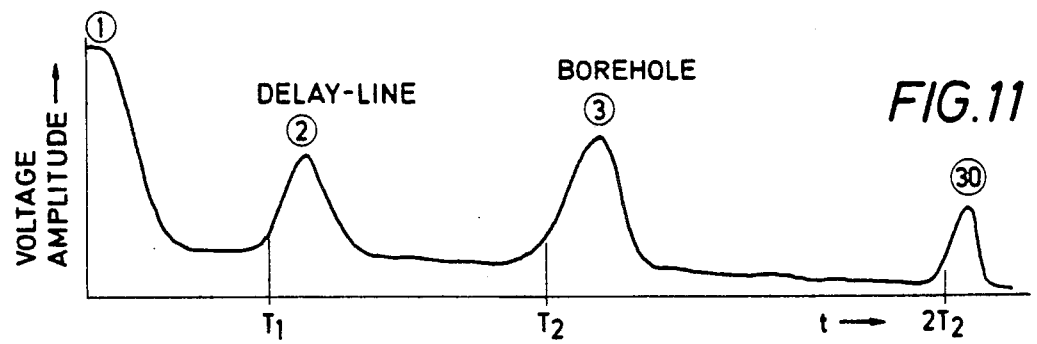
FIG. 11 illustrates that echoes may be received which are multiple reflections from the borehole.
Figure 12:
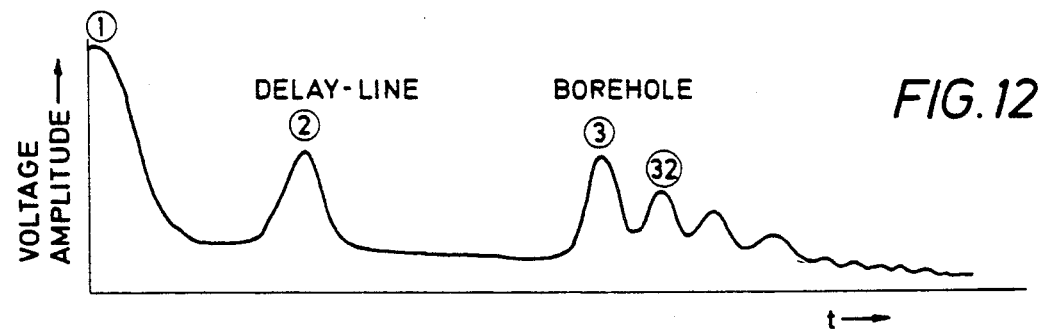
FIG. 12 illustrates late arriving noise spikes which result from true formation echoes.

FIGS. 10, 11, and 12 illustrate various conditions that the processing logic of program 200 considers. The logic flow path of FIG. 13 outlines the logic steps of the stored program 200.

FIG. 10 illustrates the output of the rectifier 174 (FIG. 3) which corresponds to the case when several distinct echoes (24), (25), (26), (28) are detected before the borehole echo (3). The emitted pulse of ceramic disk 54 is represented as amplifier saturation (1) which is electronically masked during digitization. The delay-line echo is the echo (2).

The logic step 202 of FIG. 13 identifies formation and cutting echoes occurring after delay-line echo (2). The delay-line echo (2) is the first echo, where the delay-line 70 has but one interface with the drilling fluid. The stored program 200 stores the amplitude and arrival time of each of the echoes occurring after the delay-line echo. For example, for the echo patterns of FIG. 10, echoes (24), (25), (26), (28) and (3) are stored.

The logic box 204 of FIG. 13 illustrates that noise echoes are rejected by requiring that each echo occurring at a certain time has to be above a minimum signal level for that time. Such requirement insures the separation of echoes from sensor noise. The level of acceptance decreases with time after excitation, because the sensor noise quickly decays after the excitation. In other words, the amplitude of each echo is compared with a predetermined function $A_{min}(T_N)$ where $T_N$ is the echo delay time after the excitation pulse. The processing preferably recognizes a limited number of echoes (in the range of 2 to 12). The larger echoes are saved for further processing. Applying such logic to FIG. 10, echoes (24), (25), (26), (28) and (3) will be accepted.

The next logic step depicted as logic box 206 of FIG. 13, insures that each successive echo has a decreasing amplitude with time. In other words, the amplitude of each successive echo must be smaller than that of the previous echo. If not, the previous one is discarded from the list of echoes. Such processing is based on the logic that if a large echo comes after a small one, the large echo corresponds to a larger reflector. Such larger reflector is either a large cutting or the borehole wall, but the smaller echo coming first cannot be from the borehole wall. In FIG. 10 the echo (24) will be discarded based on the criteria of logic box 206 of FIG. 13.

Each echo must be separated in time from each other echo by a certain predetermined minimum time in order to avoid multiple detections of the same echo. In FIG. 10, the echo (28) is rejected by this criteria as being a noise artifact of echo (26). Logic box 208 states the criteria.

The delay-line and borehole echo logic of the invention initially defines the echo (3) of the illustration of FIG. 10 to be the "temporary formation echo". It is the last one detected. Before the final decision that such echo is indeed the borehole echo, two additional tests are made: first, the echo must not be a double echo of the echo (26); and second, the echo (3) must not be a noise echo generated by the echo (26).

If one of these two tests is not passed by echo (3), then it is rejected and echo (26) (note that echo 28 already has been rejected) is temporarily defined as the "temporary formation echo". The same two acceptance tests are again performed for this temporary formation echo and the immediately preceding echo. If these tests are successful, the echo (26) is accepted. If not, the search continues. A final solution always exists, because as above, the "temporary formation echo" cannot be compared to a previous echo if it comes immediately after the delay-line echo.

The previous procedure may force a double formation echo to be accepted as the formation echo. To account for this possibility a test is performed on two successive echoes. This double echo acceptance test of the "temporary formation echo" verifies that this echo delay time is not approximately two times the arrival time of the previous echo. As illustrated in FIG. 11, the echo (30) is first accepted as "temporary formation echo". But its arrival time is equal to about two times the arrival time of echo (3). Accordingly, echo (30) is rejected, and echo (3) becomes the "temporary formation echo". Because there is no previous echo after the delay-line echo, echo (3) becomes the final solution as the borehole or formation echo. Such logic is illustrated as logic boxes 210, 212 where the delay time of the temporary formation echo is compared with twice the delay time of each preceding echo.

The last test that a "temporary formation echo" has to pass successfully before final acceptance is the test of additional noise due to a previous echo. Each echo increases the noise in the sensor after its arrival. This noise decays with time. This noise level can be above the minimum level for its detection time. This minimum level is determined for a "quiet" situation. Accordingly, the formation echo has to be at least above this minimum level, depending on its delay time for the case of a "quiet sensor". But in case of previous echo already detected, it has to be above the noise generated by such echo.

The most simple implementation is to insure the amplitude of the "temporary formation echo" is above a certain ratio of the previous echo amplitude. An example is shown in FIG. 12. The echo (32) represents noise generated by the echo (3). This test rejects the echo (32), and echo (3) is accepted as "temporary formation echo". This echo (3) may next be compared to previously occurring echoes if they are present, to determine which echo is finally accepted as the borehole or formation echo. Logic step 214 of FIG. 13 describes this test to determine if an echo is the result of induced sensor noise.

The amplitude of the finally accepted formation echo is stored along with its delay time from the emitted pulse and real time for the measurement. Such step is illustrated in logic box 216 of FIG. 13.

Determination of Standoff and Borehole Diameter

The borehole delay time $T_n$ stored in memory 180 according to the process of FIG. 13 provides the data necessary to determine standoff. Standoff is the distance between the front face of delay-line 70 and the wall of borehole 9. A determination of standoff and the diameter of the borehole at the depth position of the transceivers 45, 46 in the drilling string in the borehole provides valuable information to a driller. Such measurements may be stored downhole in memory 180 or passed to a MWD tool 29 for transmission to surface instrumentation 7 (FIG. 1). Both methods (downhole storage and transmission to the surface while drilling) may be performed simultaneously. The tool 20 acts as a conventional drill collar (in that it adds weight on the drilling bit) even while simultaneously performing the measurements described above and below.

The time delay of the borehole echo is inversely related to the standoff of the transceiver 45 or 46 from the borehole wall In other words, $$\text{Standoff} = \frac{2V_s}{T}$$

where $V_s$=sonic velocity and T is the measured time delay corrected for the time delay in the delay line.

Obtaining a numerical value for sonic speed in the above formula for a determination of Standoff is preferably obtained from a table for the given pressure and temperature. Sonic speed varies only a small amount with pressure and temperature in a downhole zone of interest.

The standoff measurement with one transceiver enables the statistical evaluation of the hole diameter when the tool is rotating (which is the normal case during drilling). During the rotation, the transceiver 45 sends the sonic pulse through the mud gap between the tool and the borehole wall which may vary as the tool rotates. The measured standoffs are cumulated for statistical processing, so that the average hole diameter can be calculated after several turns. The best rate of measurement is reached when several standoffs can be evaluated per second. As the typical drill string rotation speed is between 50 to 200 RPM, an average accumulation time from 10 to 60 seconds collects enough data for accurate averaging.

The average hole diameter based on only one transceiver is then calculated:

Hole diameter = Tool Diameter + 2 * average standoff.

The addition of a second transceiver 46 diametrically opposed to transceiver 45 improves the diameter measurement when the tool center is not coaxial with the well-bore during drilling. Transceiver 45 is first used to measure the standoff on its side. Then immediately thereafter the transceiver 46 is used to measure the standoff on the other side of the tool. An instantaneous firing of both transceivers is not required, as long as the tool movement in the time between the both measurements is small.

With the typical range of drill string rotation speeds, and because the wave beam width covers several degrees of the well-bore circumference (due to the diameter of the transceiver and sonic divergence), the time between the standoff evaluations performed with both transceivers can be as small as 50 milliseconds. The smaller the time, the better the final diameter evaluation. The advantage of non-simultaneous measurements is the reduction of the size the electronics module 21, because the same system can be multiplexed to control the different transceivers. The physical size of the electronics is often a major limitation for MWD type devices. Furthermore, the multiplexing and the smaller size of the electronics module required for non-simultaneous measurement reduces the instantaneous electrical power consumption, which can be critical when the tool is running from battery 150 of FIG. 3.

An approximation of the nearly instantaneous hole diameter can be calculated as:

Hole diameter = standoff 1 + standoff 2 + tool diameter,

With
Standoff 1 = standoff measured with transceiver 45
Standoff 2 = standoff measured with transceiver 46
Tool diameter − distance from face to face of the transceivers 45, 46.

This instantaneous diameter is saved in a vector. After accumulation time (which typically can be in the range of 10 to 60 sec), the diameter data stored in that vector are statistically processed to determine statistical parameters such as the average diameter, the most probable and/or an approximation of the largest diameter, or various percentiles of a Histogram. Such parameters are transmitted to the surface (or, alternatively, stored in the down-hole memory for a later use). With the statistical processing, the hole geometry determination is less sensitive to false measurements which can occur during drilling. As explained above, these false measurements, caused by cutting echoes detection instead of formation echoes detection, poor formation echo shape due to the rugosity of the formation, the misalignment of the sensor with the wall, or by a spike of noise due to the drilling operations, are eliminated for the most part by the processing steps of FIG. 13, but inevitably, a few false measurements may pass such logic processing.

Detection of Gas Influx into the Borehole While Drilling

(1) Assessing the amplitude of delay-line echoes: sonic impedance of drilling fluid As illustrated in FIGS. 6 to 12, the delay-line echo (2) is readily identified due to its occurrence shortly after the termination of the emitted sonic pulse (1). The amplitude of such delay-line echoes are stored as a function of time, in a manner similar to the storage of the borehole echo parameters of logic box 216 of FIG. 13. The amplitude of such delay-line echoes is characteristic of the reflection coefficient of the delay-line 70 and the drilling fluid in annulus 10. As explained above, the reflection coefficient depends on the sonic impedance of the drilling fluid which can be affected to a large degree by the amount of gas in the drilling fluid.

When gas enters the drilling fluid, the sonic impedance of drilling fluid decreases since gas entry reduces the drilling fluid sonic speed and density. As a result, the sonic coupling between the sensor delay-line 70 and the drilling fluid in annulus 10 varies with the reflection coefficient. In most cases, the sonic impedance of the delay-line 70 is between 2 and 3.5 Mrayls depending on its material and its operating temperature. It is typically higher than the sonic impedance of the drilling fluid which is typically between 1.5 to 3.5 Mrayls. Accordingly, in the usual case were the delay-line sonic impedance is about 3 Mrayls, the echo of the front face of the delay-line 70 increases in amplitude with an increase of gas concentration, because the difference in sonic impedance of the fluid and that of the delay-line increases.

The broadest concept of the invention is to measure and monitor the delay-line echo amplitude as a function of time during drilling. In normal drilling operations, the delay-line echo amplitude drifts slowly with time due to pressure and temperature changes down-hole. The sensor performance and the acoustic properties of the drilling fluid depend on these down-hole conditions. Such drift is small because down-hole pressure and temperature change slowly while drilling.

But gas influx occurs relatively suddenly resulting in a sudden drop (a few percent in a few minutes) of sonic mud impedance. Such change causes a rapid change of the delay-line echo amplitude. Monitoring of the rate of change of this amplitude provides a way to detect down-hole gas influx.

Additional processing can be performed to predict the amount of gas of the gas influx. This additional processing requires data concerning the sensor performance under conditions of temperature and the current mud density. Additional processing can be performed if the impedance of the delay-line can be measured, so that the front-face echo amplitude can be converted into mud impedance. Such delay-line impedance can be measured if the delay-line is constructed of two layers, so that an echo from the interface between these two layers can be detected. Assuming constant thickness of the outermost layer in contact of the fluid, the sonic speed can be calculated for this layer. The density of the outermost layer may be assumed to be constant (which is a good approximation with hard plastic or hard rubber). Then, the impedance of this layer can be calculated.

2) Assessing borehole echo amplitude: Sonic attenuation of drilling fluid

Figure 14:
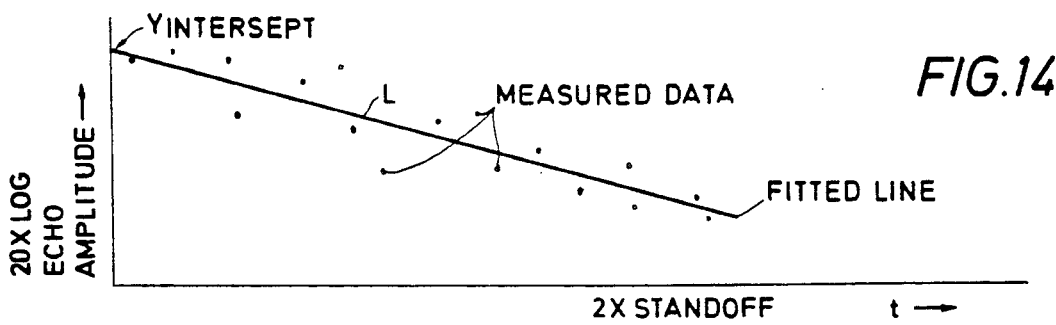
FIG. 14 illustrates graphically the determination of mud attenuation by plotting the log amplitude of borehole echoes as a function of tool standoff.

From several detected borehole echoes, the mud attenuation can be calculated by the method illustrated in FIG. 14. A line is fit between the logarithmic value of the borehole echo amplitude versus the corresponding standoff. The slope of such line is equal to the sonic attenuation in the mud.

As long as all other parameters which control the amplitude of the borehole characteristics such as rugosity, impedance, etc., remain constant over the time of measurement of the borehole amplitudes, the slope of the line defined above and illustrated in FIG. 14 is independent of the values of such parameters.

Among the parameters which affect borehole echo amplitude are the sensor performance, the excitation voltage, the attenuation in the delay-line and matching layer, the sonic coupling between the sensor and the mud, and the reflectivity of the formation. All such parameters influence the Y-intercept of the fitted line. A correlation coefficient of the data may be calculated to validate the fitting of the line L and to provide for the rejection of an erroneous calculation of mud attenuation.

Figure 15:
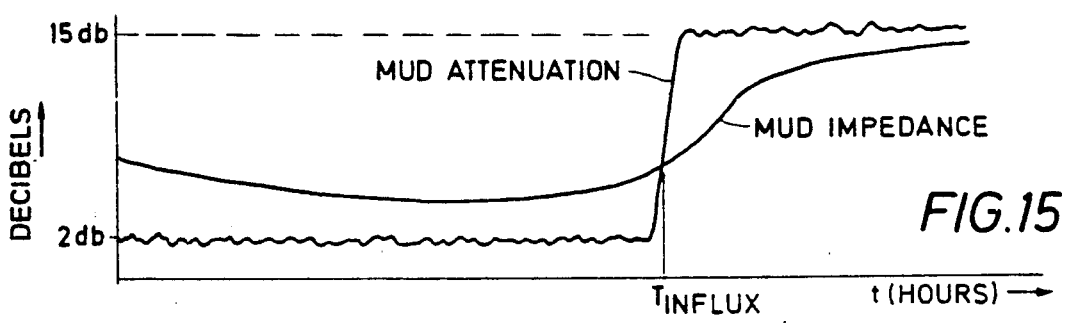
FIG. 15 illustrates the variables of mud impedance and mud attenuation in decibels plotted as a function of drilling time, with a specific illustration of the effect on such variables of gas influx into the borehole at a particular time.

A method for gas detection is illustrated in FIG. 15, where mud attenuation is plotted as a function of time. Such method may be performed by tool computer 160, or it may be performed by surface instrumentation computers in surface instrumentation 7 after amplitude data and standoff data have been transmitted to the surface. When no gas is in the drilling fluid, sonic mud attenuation is typically in the range of 1 to 5 db/cm. With a small gas influx, of the range of 0.2% void fraction of the mud, the sonic mud attenuation jumps dramatically to 8 to 15 db/c m or more at the basic sensor frequency Accordingly, such gas influx at time $T_{INFLUX}$ is detected by the mud attenuation plot of FIG. 15. Even without a reference measurement, gas influx may be determined by the change. A mud attenuation reference measurement (measured as close a possible to downhole conditions) improves the resolution of influx detection.

The increase in the mud impedance curve at time $T_{INFLUX}$ confirms the determination of gas influx as illustrated by FIG. 15.

Transmission of Signals to Surface Instrumentation for Further Processing

The parameters identified above, such as standoff, sonic impedance and mud attenuation may be determined as a function of drilling time and stored in electronic module memory 180. These data of such memory 180 as well as others, may be transmitted to surface instrumentation 7 via MWD tool 29 using the drilling fluid as a communication path. Such MWD tool and methods are conventional in the art of MWD communication.

When the mud attenuation and mud impedance signals received by surface instrumentation 7 simultaneously increase by a predetermined amount within a predetermined drilling time period, an alarm may be generated as signified by bell 7A of FIG. 1.

Various modifications and alterations in the described methods and apparatus will be apparent to those skilled in the art of the foregoing description which does not depart from the spirit of the invention. For this reason, these changes are desired to be included in the appended claims. The appended claims recite the only limitation to the present invention. The descriptive manner which is employed for setting forth the embodiments is to be interpreted as illustrative but not limitative.

What is claimed is:

1. Bore hole measurement apparatus comprising,
a tool adapted for connection in a drill string in said borehole through earth formations, said tool having a cylindrical body which when disposed in said borehole defines an annulus between a borehole wall and said body, said annulus having drilling fluid with entrained drilling cuttings disposed therein, the distance between said borehole wall and said cylindrical body defining standoff distance,
ultra-sonic transmitter means disposed in said cylindrical body for emitting an ultra-sonic transmitter pulse in said drilling fluid toward said borehole wall, said ultra-sonic pulse being reflected from said borehole wall as a borehole echo adn from said drilling cuttings toward said cylindrical body as a cuttings echo,
ultra-sonic transducer means disposed in said cylinrical body for generating a borehole echo signal representative of said borehole echo and a cuttings echo signal representative of said cuttings echo, and
logic means for distinguishing said borehole echo signal and its time delay from said cuttings echo signal, and means for generating a standoff signal representative of said standoff distance which is inversely related to said borehole echo time delay,
wherein said ultra-sonic transmitter means and said ultra-sonic transducer means includes a single transceiver in which one sensor element serves first as a sonic transmitter and later as a sonic receiver,
wherein said transceiver is disposed in said cylindrical body so that said sensor element faces laterally outwardly from said cylindrical body whereby said ultra-sonic pulses and echoes travel essentially perpendicularly between said borehole wall and said cylindrical body in said annulus, and
wherein said logic means includes
circuit means for storing echoes where each echo is defined as the approximate maximum amplitude and associated delay time of each pulse received by said sensor element after said ultra-sonic transmitted pulse has terminated.

2. The apparatus of claim 1 wherein
said drill string is rotating in said borehole, said drilling fluid with entrained drilling cuttings disposed therein is flowing in said annulus, and
wherein said apparatus further includes processing means for generating said standoff signal a plurality of times each second for a predetermined time interval and for generating from said plurality of standoff signals an average standoff signal for said time interval.

3. The apparatus of claim 2 further including
memory means for storing a tool diameter signal representative of a diameter of said cylindrical body of said tool, and
processing means for generating a hole diameter signal representative of a diameter of said borehole by adding said diameter signal to a signal equal to twice said average standoff signal.

4. The apparatus of claim 3 further including
clock means for generating a time signal, and
memory means for storing said diameter signal as a function of said time signal.

5. The apparatus of claim 3 further including
communication means for transmitting said diameter signal to surface instrumentation.

6. The apparatus of claim 1 wherein said single transceiver includes a delay line between said sensor element and said annulus, and wherein a delay-line echo is received by said sensor element as a result of said ultrasonic pulse being reflected from an interface of said delay-line and said drilling fluid in said annulus.

7. The apparatus of claim 1 wherein said logic means includes
  delay line echo elimination logic means for eliminating stored echoes having a delay time shorter than a predetermined delay time after said transmitter pulse.

8. The apparatus of claim 1 wherein said logic means includes
  noise rejection echo elimination logic means for eliminating stored echoes which are noise artifacts of previous echoes rather than reflection from said borehole or said cuttings.

9. The apparatus of claim 8 wherein said noise rejection echo elimination logic means includes
  a minimum echo amplitude function stored as a function of delay time from said transmitter pulse,
  comparison means for identifying stored echoes having amplitudes less than said minimum echo amplitude at its associated delay time, and
  means for eliminating said identified echoes from said stored echoes.

10. The apparatus of claim 1 wherein said logic means includes
  decreasing echo amplitude logic means for eliminating a stored echo, $A_M$, $T_M$, when the amplitude $A_{M+1}$ of the next in time echo, $A_{M+1}$, $T_{M+1}$, is larger than $A_M$.

11. The apparatus of claim 1 wherein said logic means includes,
  time separation logic means for eliminating a stored echo, $A_M$, $T_M$, when the time separation $T_M - T_{M-1}$ between such stored echo and a preceding stored echo, $A_{M-1}$, $T_{M-1}$ is less than a predetermined minimum time $T_{MIN}$.

12. The apparatus of claim 1 wherein said logic means includes,
  noise rejection echo elimination logic means for eliminating stored echoes which result from noise rather than reflection from said borehole or said cutting, decreasing echo amplitude logic means for eliminating a stored echo, $A_M$, $T_M$, when the amplitude $A_{M+1}$ of the next in time echo, $A_{M+1}$, $T_{M+1}$, is larger than $A_M$,
  time separation logic means for eliminating a stored echo, $A_M$, $T_M$, when the time separation $T_M - T_{M-1}$ between such stored echo and a preceding stored echo, $A_{M-1}$, $T_{M-1}$ is less than a predetermined minimum time $T_{MIN}$,
  temporary formation echo selection logic means for selecting a final echo, $A_N$, $T_N$ of said remaining stored echoes as a temporary formation echo, and
  double echo elimination logic means for identifying said temporary formation echo as a double echo if said delay time $T_N$ of said temporary formation echo is equal to approximately twice the delay time of a previous stored echo, and it such temporary formation echo is so identified, eliminating said final echo from said stored echoes, whereby a penultimate echo, $A_{N-1}$, $T_{N-1}$, becomes said temporary formation echo.

13. The apparatus of claim 12 wherein said logic means further includes
  echo induced sensor noise elimination logic means for comparing said temporary formation echo $A_N$, $T_N$, with an immediately preceding echo $A_{N-1}$, $T_{N-1}$, to identify such echo $A_N$, $T_N$ as a formation echo signal if $A_N > K^* A_{N-1}$, where K is a predetermined minimum ratio of successive amplitudes of echoes above which an echo is unlikely to be an echo induced noise pulse.

14. The apparatus of claim 13 further including control means for generating and storing said formation echo signal $A_N$, $T_N$, a plurality of times each second for a predetermined time interval and for generating from said plurality of standoff signals an average standoff signal for said time interval.

15. The apparatus of claim 14 further including
  memory means for storing a diameter signal representation of a diameter of said cylindrical body of said tool, and
  processing means for generating a hole diameter signal representative of a diameter of said borehole by adding said diameter signal to a signal equal to twice said average standoff signal.

16. Borehole measurement apparatus comprising,
  a tool adapted for connection in a drill string in said borehole through earth formations, said tool having a cylindrical body which when disposed in said borehole defines an annulus between said borehole wall and said body, said annulus having drilling fluid with entrained drilling cuttings disposed therein,
  first and second ultra-sonic transmitter means disposed diametrically opposed from each other in said cylindrical body for emitting first and second ultra-sonic transmitter pulses in said drilling fluid toward said borehole wall, the distance between said borehole wall and said cylindrical body at said first ultra-sonic transmitter means defining a first standoff distance, the distance between said borehole wall and said cylindrical body at said second ultra-sonic transmitting means defining a second standoff distance, said ultra-sonic pulses being reflected from said borehole wall as first and second borehole echoes and from said drilling cuttings toward said cylindrical body as first and second cutting echoes,
  first and second ultra-sonic transducer means disposed in said cylindrical body for generating first and second borehole echo signals representative of said first and second borehole echo signals representative of said first and second borehole echo amplitudes and time delays, and first and second cuttings echo signals representative of said cuttings echoes, and
  logic means for distinguishing said first borehole echo signal and its time delay in the presence of said first cuttings echo signal and for generating a first standoff signal representative of said first standoff distance which is inversely proportional to said time delay of said first borehole echo signal from said emitting of said first ultra-sonic transmitter pulse and for distinguishing said second borehole echo signal and its time delay in the presence of said second cuttings echo signal and for generating a second standoff signal representative of said second standoff distance which is inversely proportional to said time delay of said second borehole echo signal from said launching of said second ultra-sonic transmitter pulse,
  wherein said first and second transmitter means emit said first and second ultra-sonic transmitter pulses alternately in time with said logic means identifying said first borehole echo signal after said first ultra-sonic transmitter pulse is emitted and said logic means identifying said second borehole echo signal after said second ultra-sonic transmitter pulse is emitted, and processing means for generating a first standoff signal proportional to said time delay of said first borehole echo signal and for generating a second standoff signal proportional to said time delay of said second borehole echo signal, processing means for generating said first and second standoff signals a plurality of times each second for a predetermined time interval, and for generating from said plurality of standoff signals an average first standoff signal and an average second standoff signal for said time interval, memory means for storing a diameter signal representative of a diameter of said cylindrical body of said tool, and processing means for generating a hole diameter signal representative of a diameter of said borehole by adding said diameter signal to a said average first standoff signal and to said average second standoff signal.

17. The apparatus of claim 16 further including clock means for generating a time signal, and memory means for storing said diameter signal as a function of said time signal.

18. The apparatus of claim 16 further including communication means for transmitting said diameter signal to surface instrumentation.

19. The apparatus of claim 16 wherein said first ultra-sonic transmitter means and said first ultra-sonic transducer means and said second ultra-sonic transmitter means and said second ultra-sonic transducer means are each a single transceiver in which one sensor element serves as a sonic transmitter and as a sonic receiver.

20. Borehole measurement apparatus for identifying large gas bubble influxes into a borehole comprising a tool adapted for connection in a drill string in said borehole through each formation, said tool having a cylindrical body defining an annulus between said borehole wall and said body, said annulus having drilling fluid disposed therein, ultra-sonic transceiver means disposed in said cylindrical body for emitting an ultra-sonic pulse in said drilling fluid toward said borehole wall and for receiving ultra-sonic echo pulses reflected from said borehole wall, and a phase detector for detecting the phase of said pulses and for generating a signal indicating that an echo has high frequency oscillations which are approximately 180° out of phase from the echo pulse, such signal indicative of the sensing of a large gas bubble.

* * * * *